United States Patent
Gante et al.

[11] 3,981,887
[45] Sept. 21, 1976

[54] SULFOXIDES AND SULFONES
[75] Inventors: Joachim Gante; Hans-Adolf Kurmeier; Werner Mehrhof; Albrecht Wild, all of Darmstadt, Germany
[73] Assignee: Merck Patent Gesellschaft mit beschrankter Haftung, Darmstadt, Germany
[22] Filed: July 31, 1974
[21] Appl. No.: 493,459

[30] Foreign Application Priority Data
Aug. 4, 1973  Germany............................ 2339617

[52] U.S. Cl. ............................ 260/327 P; 260/328; 424/275; 424/276; 424/277
[51] Int. Cl.² .............. C07D 335/12; C07D 339/08; C07D 327/08
[58] Field of Search ......................... 260/327 P, 328

[56]  References Cited
UNITED STATES PATENTS
3,639,612  2/1972  De Long et al..................... 424/276

OTHER PUBLICATIONS
Maior, Chem. Abstracts 68: 12922u (1968).
Janczewski et al., Chem. Abstracts 76: 112546h (1972).

Primary Examiner—Natalie Trousof
Assistant Examiner—C. M. S. Jaisle
Attorney, Agent, or Firm—Millen, Raptes & White

[57]  ABSTRACT

Sulfoxides and sulfones of the formula

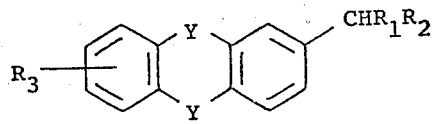

wherein $R_1$ is COOH, COOR$_4$, CH$_2$OH, or CH$_2$OR$_5$; $R_2$ is CH$_3$ or C$_2$H$_5$; $R_3$ is H, F, Cl, or Br; $R_4$ is alkyl of 1–8 carbon atoms; $R_5$ is alkanoyl of 2–4 carbon atoms; one of the Y groups is SO or SO$_2$ and the other Y group is CH$_2$, O, S, SO, or SO$_2$; and the physiologically acceptable salts thereof, which compounds possess anti-inflammatory activity, can be produced by converting in a compound of the formula

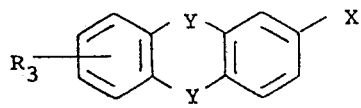

wherein X is a group convertible into the group —CHR$_1$R$_2$ wherein $R_1$, $R_2$, $R_3$, and Y have the values given above, the group X into the group —CHR$_1$R$_3$.

9 Claims, No Drawings

SULFOXIDES AND SULFONES

BACKGROUND OF THE INVENTION

This invention relates to novel sulfoxides and sulfones.

Compounds of the same general type as those of this invention are known [cf. Chem. Abstracts 68, 12922 (1968); 75, 20353 (1971)], but are less active.

SUMMARY OF THE INVENTION

In a composition aspect, this invention relates to sulfoxides and sulfones of general Formula 1

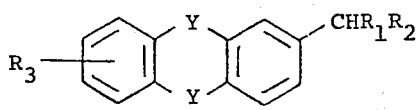

1 wherein $R_1$ is COOH, COOR$_4$, CH$_2$OH, or CH$_2$OR$_5$; $R_2$ is CH$_3$ or C$_2$H$_5$; $R_3$ is H, F, Cl, or Br; $R_4$ is alkyl of 1–8 carbon atoms; $R_5$ is alkanoyl of 2–4 carbon atoms, and one of Y is SO or SO$_2$ and the other is CH$_2$, O, S, SO, or SO$_2$, and the physiologically acceptable salts of those compounds wherein $R_1$ is COOH.

In another composition aspect, this invention relates to pharmaceutical compositions comprising an antiphlogistically effective amount per unit dosage of a novel compound of this invention in admixture with a pharmaceutically effective carrier.

In a process aspect, this invention relates to a process for the production of a compound of this invention from a compound corresponding thereto but possessing, instead of the —CHR$_1$R$_2$ group or instead of one or both Y groups, a group convertible thereto.

DETAILED DISCUSSION

The compounds of Formula 1 are:

sulfoxides and sulfones of thianthrenes (Formula 1, one Y = SO or SO$_2$, the other Y = S, SO, or SO$_2$);

sulfoxides and sulfones of thioxanthenes (Formula 1, one Y = SO or SO$_2$, the other Y = CH$_2$); and sulfoxides and sulfones of phenoxathiins (Formula 1, one Y = SO or SO$_2$, the other Y = O).

Examples of such compounds (in each case substituted in the 2-position by —CHR$_1$R$_2$) are: thianthrene-5-oxides, thianthrene-10-oxides, thianthrene-5,10-dioxides, thianthrene-5,5-dioxides, thianthrene-10,10-dioxides, thianthrene-5,5,10-trioxides, thianthrene-5,10,10-trioxides, thianthrene-5,5,10,10-tetroxides, phenoxathiin-10-oxides, phenoxathiin-10,10-dioxides, thioxanthene-10-oxides, and thioxanthene-10,10-dioxides. In several of the oxidized thianthrene derivatives, the position of the SO— and/or SO$_2$-groups could not as yet be unequivocally determined with respect to the constitution. These are referred to hereinbelow collectively as "thianthrene-5(or 10)-oxides", "thianthrene-5,5(or 10,10)-dioxides", and "thianthrene-5,5,10(or 5,10,10)-trioxides".

Of the compounds of Formula 1, preferred are the thianthrene-5(or 10)-oxides, the thioxanthene-10-oxides, the thioxanthene-10,10-dioxides, the phenoxathiin-10-oxides, and particularly the phenoxathiin-10,10-dioxides, wherein the —CHR$_1$R$_2$ group in each instance is in the 2-position.

The numbering of the positions of these compounds is according to the data in "The Ring Index", Second Edition, 1960 (Nos. 3449, 3607, and 3408).

Of the compounds of Formula 1, preferred are those wherein a. $R_1$ is COOH, COOCH$_3$, COOC$_2$H$_5$, CH$_2$OH, or CH$_2$OCOCH$_3$;

b. $R_2$ is CH$_3$;

c. $R_3$ is H. When $R_3$ is F, Cl or Br, the halogen atom preferably is at one of the two "meta" positions, i.e., the 7- or 8-position in the thianthrene and phenoxathiin derivatives, and the 6- or 7-position in the thioxanthene derivatives of Formula 1. However, the halogen atom can also be at the 6- or 9-position of the former compounds or in the 5- or 8-position of the latter.

d. $R_4$ is methyl or ethyl. $R_4$ can also be, for example, n-propyl, isopropyl, n-butyl, isobutyl, sec.-butyl, tert.-butyl, n-pentyl, isoamyl, n-hexyl, n-heptyl, n-octyl, or 2-ethylhexyl.

e. $R_5$ is acetyl. $R_5$ can also be, for example, propionyl, butyryl, or isobutyryl.

Esters which are functional and pharmaceutical equivalents of compounds of Formula 1 wherein $R_1$ is COOR$_4$ or CH$_2$OR$_5$ will be apparent to those skilled in the art, e.g., wherein $R_4$ bears a substituent or $R_5$ is aroyl, aralkanoyl or alkanoyl bearing a substituent.

In its process aspect, this invention relates to a process for the preparation of compounds of general Formula 1, wherein a. the X group of a compound of the general Formula 2

Z - X        2 wherein X is

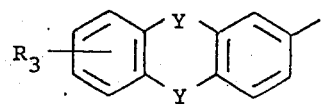

and X is a group convertible into a —CHR$_1$R$_2$ group is converted into the group —CHR$_1$R$_2$; or b. a compound of the general Formula 3a, 3b

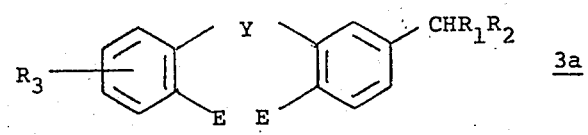

3a

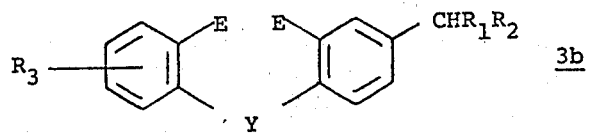

3b or a mixture thereof, wherein one of the E groups is $E_1$ and the other is $Y-E_2$ wherein $E_1$ is a residue which can be split off with $E_2$ as $E_1E_2$, and $E_2$ is H, an equivalent of an alkali or alkaline earth metal, OH, Cl, Br, or I, is cyclized by treatment with an agent which splits off $E_1E_2$; or c. in a compound of the general Formula 4

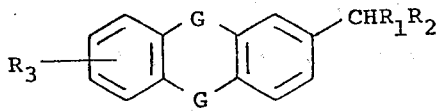

$$\underline{4}$$

wherein the G groups are alike or different and convertible into the group Y, wherein one G group may be Y, the G groups are converted to Y;

and optionally, in a thus-obtained product of Formula 1, in one or several stages, one or both of the $R_1$ and/or $R_3$ are converted into an $R_1$ and/or $R_3$ group having a different value.

In the formulae set forth above and herein below, the $R_1$ through $R_5$ and Y have the values given for Formula 1, Z and X have the values given for Formula 2, E, $E_1$, and $E_2$ have the values given for Formula 3, and G has the values given for Formula 4, unless indicated otherwise.

All of these reactions can be accomplisheed in accordance with methods known from the literature, wherein one can also make use of modifications known per se, which are not set forth in detail herein.

Suitably, the compounds of Formula 1 are prepared according to methods known from the literature by the following process:

a. a compound of the formula $Z-CHR_1M$ (2aa) (Formula 2, $X = -CHR_1M$) wherein M is MgHal or an equivalent of a metal atom or of an organometallic group and Hal is Cl, Br, or I, is reacted with a compound of the formula $$X_1-R_2 \tag{5a}$$

wherein $X_1$ is Hal or an optionally reactively functionalized hydroxy or amino group, or is reacted with a des—$HX_1$ derivative of such a compound, or a compound of the formula $Z-CHR_2M$ (2ab; = Formula 2, $X = -CHR_2M$) is reacted with a compound of the formula $X_1R_1$ (5b) or with a des—$HX_1$ derivative of such a compound, under conditions which split off $MX_1$; or b. a compound of the formula $$Z-X_2 \tag{2b}$$

(Formula 2, $X = X_2$) wherein $X_2$ is a group oxidizable to the group $-CHR_1R_2$ and corresponds especially to the group $-CHR_1R_2$ but contains instead of $R_1$ a group oxidizable to $R_1$, is treated with a dehydrogenating and/or oxidizing agent; or c. a compound of the formula $$Z-X_3 \tag{2c}$$

wherein $X_3$ is a group reducible to the group $-CHR_1R_2$ and especially a group otherwise corresponding to $-CHR_1R_2$ but additionally containing at least one reducible group and/or multiple bond, is treated with a reducing agent; or d. a compound of the formula $$Z-X_4 \tag{2d}$$

wherein $X_4$ otherwise corresponds to $-CHR_1R_2$, but contains additionally a group removable by thermolysis or solvolysis, is treated with a thermolyzing or solvolyzing agent; or e. a compound of the formula $Z-CHR_2X_1$ (2e) (Formula 2, $X = -CHR_2X_1$) or a des—$HX_1$ derivative of such a compound is reacted wih CO and/or a metal carbonyl, optionally in the presence of a reducing agent and/or a catalyst; or f. a halogenide of the formula $Z-CO-CHR_2Hal$ (2f) (Formula 2, $X = -CO-CHR_2Hal$) is treated with a strong base; or g. a compound of the formula $$Z-CHR_2-CH_2X_5 \tag{2g}$$

wherein $X_5$ is Hal or a diazonium group, is reacted with a compound of the formula $R_6OH$ wherein $R_6$ is H or $R_5$, or with a metal derivative of such a compound; or h. a compound of the formula $$Z-CHR_2-X_6 \tag{2h}$$

wherein $X_6$ is a group convertible into an $R_1$ group by solvolysis, is treated with a solvolyzing agent.

The above Formulae 2aa and 2ab, as well as 2b through 2h correspond all to Formula 2, wherein X has the values respectively indicated for the individual formulae.

In the above-mentioned compounds, M, in addition to MgCl, MgBr or MgI, can be primarily an equivalent of an alkali metal atom (e.g., Li, Na, K), of an alkaline earth metal atom (e.g., Mg, Ca), of a Cu, Cd or Zn atom, or of an organometallic group. The term "organometallic residue" encompasses organoboron residues, for example, 9-borabicyclo-[3,3,1]nonyl-(9). In the $X_1$ group, the optionally reactively functionally hydroxy or amino groups means, in particular, those groups which can be split off under the reaction conditions as $HX_1$ analogously to Cl, Br, or I, for example $NH_2$, NHA (wherein A is alkyl of 1-8, preferably 1-4 carbon atoms, e.g., methyl, ethyl, n-butyl or n-octyl), NHAr (wherein Ar is optionally substituted aryl of 6-10 carbon atoms, e.g., phenyl, 1-or 2-naphthyl), OH, AcO (wherein Ac is acyl of 1-18 carbon atoms, preferably alkanoyl of 2-10, alkylsulfonyl of 1-6, arylsulfonyl of 6-10, or aroyl of 7-10 carbon atoms, for example formyl, acetyl, caproyl, stearoyl, methanesulfonyl, hexanesulfonyl, benzene sulfonyl, 1- or 2-naphthalenesulfonyl, benzoyl, 1- or 2-naphthoyl), or an etherified OH-group of especially 1-7 carbon atoms (e.g., methoxy, benzyloxy).

The individual process variations will be explained hereinbelow.

a. Compounds of Formula 1 are obtainable, for example, by reaction of an organometallic compound of Formula 2aa or 2ab, respectively, with a halogen compound or an analog thereof, of Formula 5a, or 5b, respectively or the des—$HX_1$ derivatives thereof, especially the dehydrohalogen derivatives of these compounds, under conditions wherein $MX_1$ is split off and which correspond to the conditions for organometallic syntheses known from the literature.

Typical starting substances for this reaction are the following, for example:

Z—$CHR_1M$ (2aa): the derivatives, metalized in the α-position, for example, by Na or an $MgX_1$ group, of the sulfoxides and/or sulfones of 2-thianthrenyl-,2- or 3- thioxanthenyl-, 2- or 3-phenoxathiinyl-acetic acid, 2-(2-thianthrenyl)-ethanol, as well as those of the corresponding thioxanthene and phenoxathiin derivatives;

Z—$CHR_2M$ (2ab): the sulfoxides and/or sulfones of 1-(2-thianthrenyl)-ethyllithium, -magnesium chloride, or -magnesium bromide, 1-(2-or 3-thioxanthenyl)-ethyllithium, -magnesium chloride or -magnesium bromide, 1-(2- or 3-phenoxathiinyl)-ethyllithium, -magnesium chloride, or -magnesium bromide;

$X_1R_2$ (5a): alkyl halides, e.g., methyl chloride, bromide, or iodide, ethyl chloride, bromide or iodide, and the corresponding alcohols and the reactive esters thereof, e.g., the sulfuric acid and sulfonic acid esters, such as the p-toluene-sulfonates, e.g., dimethyl sulfate or ethyl p-toluenesulfonate;

$X_1R_1$ (5b): carbonic acid derivatives, such as orthocarbonic acid tetraethyl ester, $CO_2$, diethyl carbonate, ethyl chloroformate.

The starting compounds 2aa and 2ab are producible in a conventional manner, for example by metalizing the corresponding halogen compounds, for example with metallic Na, Li or Mg, NaH, $NaNH_2$, alkyl- or aryllithium compounds, e.g., butyllithium or phenyllithium.

Suitable solvents for the reactions of 2aa and/or 2ab with 5a and/or 5b are, for example, ethers, e.g., diethyl ether, diisopropyl ether, 1,2-dimethoxyethane, tetrahydrofuran (THF), dioxane, and mixtures with each other, or with hydrocarbons, e.g., hexane, benzene, toluene or xylene; amides, e.g., dimethylformamide (DMF), hexamethylphosphoric triamide (HMPA), sulfoxides, e.g., dimethyl sulfoxide (DMSO). The reaction temperatures range normally between about $-20°$ and $180°$, preferably between $0°$ and $70°$, and the reaction times are between 0.5 and 72 hours.

Carboxylic acids of Formula 1($R_1$ = COOH) are obtained, for example, by the reaction of compounds 2ab with $CO_2$. For this purpose, a dry $CO_2$ stream can be introduced into the cooled solution of the organometallic compound, or this solution can be poured onto solid $CO_2$. Preferably, a Grignard compound of the formula Z—$CHR_2$—MgHal is utilized. It is also possible to utilize an organometallic compound 2aa or 2ab wherein M is an organoboron group, especially a 9-borabicyclo[3,3,3]nonyl-(9) group. These starting materials can be obtained, for example, by reacting the corresponding organolithium compounds with 9-borabicyclo[3,3,1]nonane in an ether at temperatures of between about $-10°$ and $+20°$ and subsequent acidification. These compounds normally are not isolated. The actual reaction of these organoboron compounds with the compounds of Formula 5a or 5b takes place advantageously with the addition of a lower tertiary alkanol and an excess of a lower alkali metal tert.-alkoxide, preferably K-tert.-butylate or -pentylate, at temperatures of between about $-10°$ and $+20°$.

b. Compounds of Formula 1 can also be prepared by dehydrogenation or oxidation of compounds of Formula 2b.

Suitable starting substances are, for example, those wherein $R_7$ is H or any desired organic residue, preferably A, Ar, CN or COOH, since the portion of the molecule bearing the $R_7$ group is removed by oxidation and thus the value for $R_7$ is not critical, and X is: —$CHR_2$—CHO, —$CHR_2$—CH=$CHR_7$, —$CHR_2$—CHOH—CHOH—$R_7$, —$CHR_2$—CHOH—CO—$R_7$, —$CHR_2$—CHOH—$COOR_7$, —$CHR_2$—CHOH—$CHNH_2R_7$, —$CHR_2C{\equiv}C$—$R_7$, —$CHR_2$—CO—$R_7$, —$CHR_2$—$CH_2$—$R_8$ (wherein $R_8$ is a hydrogen boronide, boron alkyl, aluminum alkyl, an alkali metal, or an alkaline earth metal halide) or —$CR_2$=$R_9$ (wherein $R_9$ is =$CH_2$, (OH,$CH_3$), or the group —O—$CH_2$—).

In accordance with the oxidation methods described in the literature, the following can, for example, be used as the oxidizing agents: air or oxygen, preferably with the addition of catalysts, such as Mn, Co, Fe, Ag, $V_2O_5$; silver oxide, optionally also together with copper oxide; $H_2O_2$, preferably in the presence of an alkali; organic peracids, e.g., peracetic acid, perbenzoic acid, perphthalic acid; potassium permanganate in water, acetone or pyridine and/or in an acidic, neutral, or alkaline medium, optionally with the addition of $MgSO_4$; chromic acid or $CrO_3$, for example in acetic acid, acetone, or in aqueous acetone in the presence of sulfuric acid; $HNO_2$ and the salts thereof; $HNO_3$ and the salts thereof, e.g., 2–68% strength nitric acid, optionally under pressure (up to 100 atmospheres); nitrogen oxides; HClO or the salts thereof, e.g., NaClO; $MnO_2$, for example in dilute sulfuric acid or in a suspension in inert organic solvents; $PbO_2$; lead tetraacetate, e.g., in acetic acid or benzene, optionally with the addition of pyridine; $SeO_2$; N-halogen amides, e.g., N-bromosuccinimide, for example in acetic acid/sodium acetate or in pyridine; m-nitrobenzenesulfonic acid; $H_5IO_6$ and the salts thereof; ozone; $NaBiO_3$; a mixture of sulfur and an anhydrous primary or secondary amine, e.g., morpholine.

Suitable solvents for these oxidations are, for example, water and/or aqueous alkaline solutions; carboxylic acids, e.g., acetic acid; alcohols, e.g., methanol, ethanol, isopropanol or tert.-butanol; ethers, e.g., diethyl ether, THF, dioxane; ketones such as acetone; hydrocarbons, e.g., benzene; amides, e.g., DMF or HMPA: sulfoxides, e.g. DMSO. Also advantageous are mixtures of these solvents, e.g., mixtures with water. The temperatures during the oxidation range between $-30°$ and $300°$, depending on the method employed.

The starting compounds of the formula Z—$CHR_2$—$CH_2$——$R_8$ need not be isolated in the pure form but can be oxidized directly in the reaction mixture wherein they were prepared. In one form of this mode of operation, an ethylene derivative of the formula Z—$CR_2$=$CH_2$ is first reacted with diborane. To conduct this process, for example, a $B_2H_6$ solution or a complex boron hydride, e.g., $NaBH_4$, and a Lewis acid, e.g., $B_3$ etherate, is added to a solution of the olefin in THF or di-or triethylene glycol dimethyl ether at temperatures of between about $-80°$ and the boiling point of the solvent, and the thus produced trisubstituted borane is oxidized, optionally after decomposing the excess complex hydride with water. If the oxidation is carried out, for example, with $H_2O_2$ with the addition of a base, preferably at temperatures of between 20° and 60°, alcohols are obtained (1, $R_1 = CH_2OH$). Oxidation with an excess of $CrO_3$, preferably in aqueous acetic acid at about 0°–40°, results, after reaction times of about 1–48 hours, in the production of carboxylic acids (1, $R_1 = COOH$). In place of the diborane, it is also possible to use alkyl aluminum compounds which can be subjected to addition and oxidative splitting in an analogous manner.

Furthermore, it is possible to produce, from the halogenides of the formula $Z-CHR_2-CH_2-Hal$, with alkali metals, preferably Li, or an alkaline earth metal, preferably Mg, metal compounds and metal halide compounds of the formula $Z-CHR_2-CH_2-M$ which are then treated with an oxidizing agent for conversion into compounds of Formula 1 ($R_1 = CH_2OH$). For example, oxygen is conducted through a solution of a Grignard compound of the formula $Z-CHR_2-CHR_2-MgHal$ in an inert solvent, e.g., ether, THF or dioxane, at temperatures of between about 40° and 100°. After the usual working-up operation, alcohols of the formula $Z-CHR_2-CH_2OH$ are obtained.

Furthermore, a compound of the formula $Z-CR_2=R_9$ can be treated with sulfur and with an anhydrous amine, preferably morpholine, at an elevated temperature, preferably at least 100°, until a thioamide has been formed. The thus-obtained thioamide of the formula $Z-CHR_2-CSNR_{10}$ (wherein the $R_{10}N$ group corresponds to the amine $R_{10}NH$ utilized in the reaction) can be hydrolyzed to the corresponding carboxylic acid (1, $R_1 = COOH$). It is not absolutely necessary to isolate the thioamide from the reaction mixture.

c. Compounds of Formula 1 are also obtainable by the reduction of compounds of Formula 2c. Typical compounds of the Formula 2c are, for example, those of the formula $Z-CR_1=R_{11}$ (2ca) wherein $R_{11}$ is $=CH_2$ or $=CHCH_3$; of the formula $Z-CR_2=R_{12}$ (2cb) wherein $R_{12}$ is (H,CHO), $=CHOR_5$, (H,CN), (H,$CH_2OR_{13}$), (H, COHal), (H, $CON_3$), (H, $CONH_2$), (H,CO—O—CO—OA),

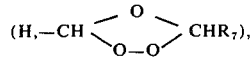

or —O—$CH_2$, and $R_{13}$ is a group which can be split off by hydrogenolysis, e.g., benzyl, diphenylmethyl, triphenylmethyl, p-methylbenzyl, 2-picolyl, or carbobenzoxy; or of the formula $Z-CR_1R_2-R_{14}$ (2cc) wherein $R_{14}$ is a group which can be removed by hydrogenolysis, especially OH, OAc, Hal, SH, $NH_2$, aralkyloxy, or aralkylamino of respectively up to 10 carbon atoms.

The reduction of these starting substances can be effected suitably by catalytic hydrogenation or by chemical methods.

The starting compounds can be treated, for example, in the presence of a catalyst with hydrogen at pressures of between 1 and 200 atmospheres and at temperatures of between about $-80°$ and 200°, preferably between 20° and 100°. Advantageously, the hydrogenation is conducted in the presence of an inert solvent, e.g., water, aqueous sodium hydroxide solution, a lower alcohol, e.g., methanol, ethanol, isopropanol, n-butanol, an ester, e.g., ethyl acetate, an ether, e.g., THF or dioxane, a carboxylic acid, e.g., acetic acid or propionic acid. It is also possible to utilize solvent mixtures. For purposes of hydrogenation, the free compounds 2c can be used, or a corresponding salt thereof, for example the sodium salt. Basically, the hydrogenation can be carried out in an acidic, neutral, or basic pH range. Suitable catalysts are, for example, noble metal, nickel and cobalt catalysts. The noble metal catalysts can be provided on supports (e.g., on charcoal, calcium carbonate or strontium carbonate), as oxide catalysts, or as finely divided metal catalysts. Preferred are platinum and palladium. Other examples are ruthenium and rhodium. Nickel and cobalt catalysts are suitably employed as Raney metals, nickel also on kieselguhr or pumice as the supports. Also suitable is copper-chromiun oxide, which achieves simultaneously a reduction of any ester groups which may be present to the alcohol state. Ethers of the formula $Z-CHR_2-CH_2OR_{13}$ are preferably split by hydrogenolysis on a Pd catalyst, e.g., Pd charcoal.

Another suitable reducing method is the reaction with nascent hydrogen. The latter can be generated, for example, by the treatment of metals with acids or bases. Thus, zinc/acid, zinc/alkaline solution, iron/acid, tin/acid systems can be used, for example. Suitable acids, for instance, hydrochloric acid or acetic acid. Also sodium or another alkali metal in a lower alcohol, e.g., ethanol, isopropanol, n-butanol, amyl alcohol, isoamyl alcohol, or in phenol, or an aluminum-nickel alloy in an alkaline-aqueous solution, optionally with the addition of methanol, or sodium amalgam or aluminum amalgam in an aqueous-alcoholic or aqueous solution are feasible for the production of nascent hydrogen. With this reduction method, temperatures of between about 0° and about 150°, preferably between 20° and the boiling point of the solvent are used.

Other suitable reducing agents are metal hydrides, especially complex metal hydrides, for example, lithium aluminum hydride, sodium borohydride, e.g., in the presence of aluminum chloride or of lithium bromide, calcium borohydride, magnesium borohydride, sodium aluminum hydride, lithium and sodium alkoxyaluminum hydrides, e.g., lithium diethoxy- or triethoxyaluminum hydride, lithium tri-tert.-butoxyaluminum hydride, sodium triethoxyaluminum hydride, sodium trialkoxyborohydrides, e.g., sodium trimethoxyborohydride. Also suitable are dialkylaluminum hydrides, for example diisobutylaluminum hydride, as the reducing agents. These reductions are suitably conducted in the presence of an inert solvent, for example, an ether, e.g., diethyl ether, THF, dioxane, 1,2-dimethoxyethane, or diglyme. Sodium borohydride can also be used in an aqueous or aqueous-alcoholic solution. The reaction takes place advantageously at temperatures of between $-80°$ and $+100°$, especially between 20° and the boiling point of the solvent used. This reaction can also be carried out under an inert gas atmosphere (for example $N_2$ or argon).

Another reducing agent which can be used especially for the removal of a tertiary OH-group in a starting compound of the formula $Z-CR_1R_2-OH$ is tin(II) chloride. This reducing agent is used primarily in the form of its dihydrate in an aqueous, aqueous-alcoholic, or aqueous-acidic solution, for example in the presence of acetic acid and/or hydrochloric acid at temperatures of between about 0° and 120°.

Another reducing agent is hydriodic acid, optionally with the addition of phosphorus and/or solvents, e.g., acetic acid, preferably at temperatures of between 100° and the boiling temperature. It is also possible to generate hydrogen iodide in situ, for example by employing a mixture of KI, red phosphorus, and phosphoric acid as the reducing agent, advantageously at temperatures of between 100° and 150°. By this method, tertiary hydroxy groups in compounds of the formula $Z—CR_1R_2—OH$ can be removed, in particular.

Other suitable reducing agents are, for example, sodium dithionite in an alkaline or ammoniacal solution; iron(II) hydroxide; hydrogen sulfide and the derivatives thereof, especially metal hydrogen sulfides, metal sulfides and metal polysulfides; $SO_2$ and the derivatives thereof, e.g., bisulfites and sulfites.

It is also possible to replace Hal atoms by hydrogen, which is done by converting the corresponding Hal compounds into the associated organometallic compounds, e.g., Grignard compounds, which are then hydrolyzed with water or dilute acid.

By the aforementioned methods, it is also possible to reduce several reducible groups in a given starting substance, wherein the compounds of Formula 2c are obtained as intermediate stages which do not have to be isolated. Furthermore, a group $R_1$ and/or $R_3$ present in the starting compound can be reduced to another group $R_1$ and/or $R_3$. In this case, the reaction conditions must be selected, in accordance with the data in the literature, so that the sulfoxide and/or sulfone groups contained in the starting substances 2c are not simultaneously attacked during the reduction.

d. Compounds of Formula 1 can also be obtained by thermolysis or solvolysis of compounds of Formula 2d.

Additional groups in the $X_4$ groups which can be removed by thermolysis or solvolysis are, in particular, carboxyl groups, which can be eliminated by decarboxylation.

It is also possible to split off acyl groups, particularly acetyl groups, by treatment with a strong alkali (acid cleavage). The oxo-group in 2-oxocarboxylic acids can also be removed, for example, in the form of carbon monoxide.

For the decarboxylation, malonic acid derivatives of the formula $Z—CR_1R_2—COOH$ are suitable, for example, wherein $R_1$ is preferably COOH or $COOR_4$. They are obtainable, for example, by condensation of an acetic acid ester of the formula $Z—CH_2—COOR_4$ with an oxalic acid dialkyl ester to form the corresponding diester of 3-oxosuccinic acid. Decarbonylation of these compounds produces malonic esters which can be alkylated, in the form of their sodium derivatives, with a compound of the formula $R_2—Hal$. The thus-obtained diesters of the formula $Z—CR_2(COOR_4)_2$ can subsequently be saponified, optionally partially.

The decarboxylation reaction can be conducted as described in the literature, for example by dry heating until the evolution of $CO_2$ has ceased, also under reduced pressure, or by heating in a solvent, e.g., water, ethanol, dioxane or xylene to temperatures of between 50° and 300°. It is also possible to split off $CO_2$ by heating with acids, e.g., a mixture of aqueous hydrochloric acid and acetic acid.

For the acid cleavage, especially suitable are keto esters of the formula $Z—CR_2Ac—COOR_4$, wherein Ac is preferably acetyl or benzoyl. These keto esters are obtainable, for example, by the condensation of esters of the formula $AcOR_4$, especially the alkyl esters of acetic acid or benzoic acid, respectively, with esters of the formula $Z—CH_2COOR_4$. The thus-produced keto esters of the formula $Z—CH(COOR_4)—Ac$ can subsequently be alkylated, thus obtaining compounds of the formula $Z—CR_2(COOR_4)—Ac$. The acid cleavage takes place normally by treatment with a strong base, e.g., NaOH, KOH or $Ca(OH)_2$, in a solvent, e.g., water, lower alcohols, e.g., methanol or ethanol, ethers, e.g., diethyl ether, THF, dioxane, hydrocarbons, e.g., benzene, or mixtures thereof. The reaction temperatures range between about $-10°$ and 200°. If it is desired to obtain the free carboxylic acids of Formula 1 ($R_1$ = COOH), the reaction mixture is preferably heated for several hours to temperatures of between about 60° and 100°.

e. Compounds of Formula 1 can also be obtained by the carbonylation of compounds of the Formula 2e or the des—$HX_1$ derivatives thereof, optionally in the presence of a catalyst.

Suitable starting substances for the carbonylation are, for example, compounds of the formulae $Z—CHR_2—Cl$, $Z—CHR_2—Br$, $Z—CHR_2—I$, $Z—CHR_2—OH$, as well as $Z—CH=R_{11}$, such as the sulfoxides and sulfones of 1-(2-thianthrenyl)-ethyl chloride, bromide or iodide, 1-(2-thianthrenyl)-ethanol, 2-vinylthianthrene, and those of corresponding 2- or 3-thioxanthenyl and/or 2- or 3-phenoxathiinyl derivatives.

The carbonylation can be achieved, as described in the literature, by the effect of gaseous CO, preferably under pressures of up to 700 atmospheres and at temperatures of up to 300°, with the addition of a heavy metal catalyst. It is also possible to treat the starting material 2e with CO in the form of a heavy metal carbonyl. It is also possible to produce the CO required for the carbonylation directly in situ from a mixture of formic acid and a mineral acid, e.g., concentrated sulfuric acid.

Compounds of the formula $Z—CHR_2—Hal$, $Z—CHR_2—OH$ or $Z—CH=R_{11}$ can suitably be reacted with a heavy metal carbonyl, such as nickel carbonyl, wherein the starting materials are preferably the halogen derivatives $Z—CHR_2—Hal$, an alkali metal tert.-alcoholate is added as the catalyst, and a tertiary alcohol, preferably tert.-butanol, is employed as the solvent. Advantageous alkali metal alcoholates are, in particular, the sodium, potassium, and lithium derivatives of the tertiary alkanols, e.g., sodium, potassium and lithium tert.-butylate. The reaction temperatures range between about 0° and about 120°, preferably between 30° and 100° and the reaction times range between 1 hour and about 4 days. Under these conditions, the tertiary alkyl esters of the corresponding carboxylic acids of the Formula 1 ($R_1$ = COOH) are obtained, which need not be isolated, but can be saponified to the free acids in situ.

In another mode of operation, the compound 2e, preferably $Z—CH=R_{11}$ or $Z—CHR_2—OH$, is reacted with the heavy metal carbonyl, preferably nickel carbonyl, advantageously in an inert solvent, e.g., THF, dioxane, acetone, in the presence of water. In this reaction, an inorganic acid, e.g., HCl, $H_2SO_4$, HBr, HI, $H_3PO_4$, can be present. The reaction temperatures range, for example, between about 20° and about 100°. The reaction can be accelerated by irradiation, for example with a mercury vapor lamp. Depending on the conditions, the reaction takes about 2 hours to 2 days.

When using formic acid/sulfuric acid, the starting substances are advantageously vinyl compounds of the formula Z—CH=CH$_2$ or carbinols of the formula Z—CHR$_2$—OH. The starting compounds are reacted, for example, at temperatures of about 0° to 40° with a mixture of formic acid and concentrated sulfuric acid, which can contain 0–50% of acetic acid or trifluoroacetic acid. Reaction times of between 1 minute and 4 hours are required.

Carbonylation with gaseous CO takes place suitably under a pressure of 100–700 atmospheres in an inert solvent, advantageously a lower alcohol, e.g., methanol, ethanol, propanol, isopropanol, n-butanol, n-pentanol, n-hexanol or a cycloalkanol, e.g., cyclohexanol. Suitable catalysts are, for example, nickel or cobalt carbonyls or halogenides, palladium dichloride, rhodium trichloride, or bis(triphenylphosphine)palladium dichloride.

f. Haloketones of the formula Z—CO—CHR$_2$—Hal, which can be produced by Friedel-Crafts acylation of the basic thioethers with haloacyl halides CHR$_2$Hal—COHal, e.g., 2-chloropropionyl chloride, and subsequent oxidation, can be rearranged into acids of the formula Z—CHR$_2$—COOH in accordance with the Favorskii method described in the literature, for example with a strong base, e.g., NaOH, in boiling toluene or xylene, or by heating in an aqueousethanolic silver nitrate solution.

g. Compounds of Formula 1 (R$_1$ = CH$_2$OH or CH$_2$OR$_5$) are also obtained by subjecting a halogen compound of the formula Z—CHR$_2$—CH$_2$Hal (2g, X$_5$ = Hal) to hydrolysis or acidolysis, or by reaction with a metal salt, e.g., sodium acetate.

Thus, it is possible, for example, to obtain alcohols of the formula Z—CHR$_2$—CH$_2$OH by saponifying a halogen compound of the formula Z—CHR$_2$—CH$_2$Hal in an aqueous or aqueous-alcoholic solution or suspension, optionally with the addition of a solubilizer, e.g., alcohol, glycol or polyglycol ether. Preferred saponifying agents are alkalis, e.g., NaOH or KOH. However, it is also possible to use slurries of Ca(OH)$_2$, Pb(OH)$_2$ or AgOH. The saponification is ordinarily conducted at an elevated temperature, for example at the boiling temperature of the solvent. However, the halogenide can also be reacted in a non-aqueous medium, by agitating a solution thereof in an inert solvent, such as, for example, acetone, ether, THF, acetonitrile or benzene, with suspended AgOH or Pb(OH)$_2$ under boiling.

Esters of the formula Z—CHR$_2$—CH$_2$OR$_5$ are produced by boiling the compounds of Formula 2g in an aqueous, aqueous-alcoholic, or alcoholic solution with alkali metal salts of the carboxylic acids to be esterified. If it is desired to obtain acetates of the formula Z—CHR$_2$—CH$_2$OCOCH$_3$, a halogenide of the formula Z—CHR$_2$—CH$_2$Hal can be reacted with anhydrous sodium acetate in acetic acid at the boiling point. It is also possible to heat a halogen compound of the formula Z—CHR$_2$—CH$_2$Hal with a suspension of the silver salt or lead salt of the acid to be esterified, in an inert solvent, e.g., ether, acetone, chloroform, THF or benzene, at the boiling point.

Diazonium compounds of Formula 2g (X$_5$ = a diazonium group) are produced by the treatment of amines of the formula Z—CHR$_2$—CH$_2$NH$_2$ with nitrous acid or a derivative thereof, such as, for example, alkyl nitrites or NOCl. They are split, in accordance with methods known per se from the literature, into alcohols of the formula Z—CHR$_2$—CH$_2$OH in the presence of water. Advantageously, an aqueous solution of NaNO$_2$ can be combined with a mineral or acetic acid solution of the amine at temperatures of 0°–100°, and the reaction can be terminated by heating. If the reaction is carried out in the presence of an acid, e.g., acetic acid, the reaction products are also esters of the formula Z—CHR$_2$—CH$_2$OR$_5$.

h. Compounds of Formula I are also obtained by solvolysis, preferably hydrolysis, in accordance with methods disclosed in the literature, of compounds of Formula 2h, which are preferably nitriles of the formula Z—CHR$_2$—CN, producible, for example, by reacting the corresponding halogenides with KCN. Also suitable as compounds 2h are: esters (X$_6$ = an esterified COOH— or CH$_2$OH-group), acid halogenides (X$_6$ = COF, COCl, CoBr); ortho esters (X$_6$ = C(OA)$_3$); acid anhydrides (X$_6$ = COOAcyl, wherein Acyl is the acyl radical of a carboxylic acid of up to 28 carbon atoms, preferably Z—CHR$_2$—CO); acid amides (X$_6$ = CONH$_2$, CONHA, CON(A)$_2$ or CONHAr); hydroxamic acids (X$_6$ = CONHOH); acid hydrazides (X$_6$ = CONHNH$_2$ or CONHNHA); acid azides (X$_6$ = CON$_3$); imino ethers (X$_6$ = C(OA)=NH); acid amidines (X$_6$ = C(=NH)NH$_2$); acid hydrazidines (X$_6$ = C(NH$_2$)=NNH$_2$ or C(NHNH$_2$)=NH); thioacids (X$_6$ = CSOH or COSH); thioacid esters (X$_6$ = CSOA or COSA); thioacid amides (X$_6$ = CSNH$_2$, CSNHA or CSN(A)$_2$); ethers (X$_6$ = an etherified CH$_2$OH group, particularly CH$_2$OA or CH$_2$OAr). In the above functional groups, the A groups, which can be alike or different, have the values given above.

Solvolysis, especially hydrolysis, can be conducted in an acidic, neutral, or alkaline medium at temperatures of between about −20° and about 200°, preferably between room temperature and the boiling temperature of the selected solvent. Suitable acidic catalysts are, for example, hydrochloric, sulfuric, phosphoric or hydrobromic acid. Advantageous alkaline catalysts are, e.g., sodium hyroxide, potassium hydroxide or calcium hydroxide, sodium carbonate or potassium carbonate. Water is the preferred solvent. Other preferred solvents are lower alcohols; ethers, e.g., THF, dioxane; amides, e.g., DMF; sulfones, e.g., tetramethylenesulfone; acetic acid; or mixtures thereof, especially the mixtures which contain water.

These ethers are suitably split by treatment with HBr or HI in an aqueous or acetic solution, by heating with Lewis acids, such as AlCl$_3$, or boron trihalides, or by melting with pyridine hydrohalides or aniline hydrohalides at about 200°.

Esters of Formula 1 (R$_1$ = COOR$_4$ or CH$_2$OR$_5$) are obtainable by solvolyzing compounds of Formula 2h wherein X$_6$ is a thioester, imino ether, oximinoether, hydrazone ether, thioamide, amidine, amidoxime, or amide hydrazone group, with water or a dilute aqueous base or acid, e.g., ammonia, NaOH, KOH, Na$_2$CO$_3$, K$_2$CO$_3$, HCl, H$_2$SO$_4$, with the addition of the respective alcohol and splitting off of hydrogen sulfide, ammonia, amines, hydrazines derivatives, or hydroxylamine at temperatures of between about 0° and 100°.

Compounds of Formula 1 are also obtainable by splitting off, from a compound of Formula 3a or 3b, a fragment of the formula E$_1$—E$_2$. One of the two groups E in Formula 3a (or 3b, respectively) is a phenolic hydroxy group or a mercapto group (which can also be present in the form of a metal salt derived therefrom, e.g., a phenolate or thiophenolate, preferably in the form of a sodium salt), or sulfonic acid or sulfonic acid ester group, or a sulfonyl halogenide derived therefrom, e.g., —$SO_2Cl$, and the other of the two groups E is, for example, hydrogen, Hal, preferably Cl or Br, an amino group, or a free or functionalized, e.g., etherified or esterified, OH— or SH—group. The compound $E_1$—$E_2$ to be split off can accordingly represent, for instance, water, ammonia, hydrogen halide, such as HCl or HBr, hydrogen sulfide. Depending on the constitution of the starting compounds, the agents utilized to split off $E_1$—$E_2$ are dehydration agents and/or acids or Lewis acids, e.g., $AlCl_3$, $ZnCl_2$, $P_2O_5$, polyphosphoric acid, or bases, NaOH, KOH, $Ca(OH)_2$ or $K_2CO_3$, optionally in the presence of a catalyst, for example, a heavy metal, e.g., copper, preferably in pulverized form. The splitting-off step can be effected in the presence of an additional inert, preferably high-boiling solvent, e.g., in the presence of xylene, tetrahydronaphthalene, or tetrachloroethane. It is also possible to operate in the absence of a solvent. The reaction temperatures range between about 0° and about 250° and are preferably between 80° and 220°.

It is also possible to conduct the reaction so that the starting material 3a and/or 3b is not isolated, but instead is produced in situ in the reaction mixture. Thus, there can be employed as a starting compound, for example, a compound which otherwise corresponds to Formula 3a or 3b, but wherein both groups E are amino groups which are subsequently diazotized and hydrolyzed. As the intermediate product, which is not isolated, a diphenol is obtained (3a and/or 3b, both groups E = OH), which is then dehydrated by heating in an acidic solution.

Furthermore, the compounds of Formula 1 can be produced by converting the group(s) G in a compound 5 into the group(s) Y.

A preferred process for preparing the compounds of Formula 1 is the single- or multistage oxidation of the corresponding thioethers (thianthrenes, thioxanthenes, and/or phenoxathiins) of Formula 4 wherein one G = S and the other G = S,O or $CH_2$. These starting compounds are obtainable in a manner known per se from the basic constituents of the general formula $Z'$—H (wherein $Z'$ is a 2-thianthrenyl, 2-or 3-thioxanthenyl, or 2- or 3-phenoxathiinyl, optionally substituted by an F, Cl or Br atom), by acylation with ethoxalyl chloride in the presence of $AlCl_3$ to form the glyoxylic acid esters of the formula $Z'$—CO—$COOC_2H_5$, reaction with an organometallic compound of the formula $R_2M$, hydrolysis to the tertiary hydroxy esters of the formula $Z'$—$CR_2(OH)$—$COOC_2H_5$, and reduction with $SnCl_2$ to the esters $Z'$—$CHR_2$—$COOC_2H_5$ (4, $R_1$ = $COOC_2H_5$), which can be converted by further hydrolysis, reduction and optionally further secondary reactions, into the remaining starting compounds of Formula 4.

Depending on the reagent selected and the conditions employed, the oxidation is conducted to obtain the corresponding sulfoxides (at least one of Y = SO) or the corresponding sulfones (at least one of Y = $SO_2$) according to methods known from the literature, and the reaction conditions can be readily derived in detail from the literature as well. If it is intended, for example, to obtain the sulfoxides, the oxidation is carried out, for example, with hydrogen peroxide, peracids, Cr(VI) compounds, e.g., chromic acid, nitric acid, nitrous gases, $N_2O_3$, halogens, e.g., chlorine, hypochlorites, $KMnO_4$, N-bromosuccinimide, 1-chlorobenzotriazole, Ce(IV) compounds, e.g., $(NH_4)_2Ce(NO_3)_6$, negatively substituted aromatic diazonium salts, e.g., o- or p-nitrophenyldiazonium chloride; or electrolytically under relatively mild conditions and at relatively low temperatures (about −80° to +100°). In contrast thereto, if the sulfones are to be produced, the same oxidizing agents are utilized under more vigorous conditions and/or in an excess, and also normally at higher temperatures. In these reactions, the customary inert solvents can be employed or the process can be conducted without solvents. Examples of suitable inert solvents are water, aqueous mineral acids, aqueous alkali solutions, lower alcohols, e.g., methanol or ethanol, esters, e.g., ethyl acetate, ketones, e.g., lower carboxylic acids, e.g., acetic acid, nitriles, e.g., acetonitrile, hydrocarbons, e.g., benzene, chlorinated hydrocarbons, e.g., chloroform or $CCl_4$.

A preferred oxidizing agent is 30% strength aqueous hdyrogen perioxide. This compound produces sulfoxides when using a stoichiometric amount in a solvent, e.g., acetic acid, acetone, ethanol or aqueous sodium hydroxide solution, at a temperature of between −20° and 100°, and produces sulfones when used in an excess, at higher temperaturea and preferably in acetic acid or in a mixture of acetic acid and acetic anhydride. In the thianthrene series, it is possible by means of the respectively stoichiometric amounts of this oxidizing agent to produce the monosulfoxides, disulfoxides, the trioxides (monosulfoxide-monosulfones), and disulfones. In this procedure, the other reaction conditions are changed only slightly. The thianthrene monosulfones are obtainable from the trioxides by reduction with HBr in acetic acid at room temperature or with zinc dust in boiling acetic acid.

A further possibility for producing the sulfoxides is by treating the thioethers with chlorine, e.g., in moist benzene or in acetic acid. The dichloro compounds, produced as intermediates, are very readily converted into the sulfoxides by hydrolysis.

It is also possible to oxidize sulfoxides obtained under the above optional conditions to the sulfones under more vigorous conditions, in which case the sulfoxides need not be isolated. Furthermore, the starting compounds 4 can be prepared in situ using preliminary products in the oxidation reaction which contain, in place of the desired $R_1$ group, another group of a lower oxidation stage.

Thus, it is possible, for example, to oxidize thioethers of Formula 4 (one G = S, $R_1$ = $CH_2OH$) in one operating step to the corresponding sulfoxides and/or sulfones 1 ($R_1$ = COOH) via the acids of Formula 4 (one G = S, $R_1$ = COOH), which are not isolated.

Optionally, in a thus-obtained product of Formula 1, one or both of the $R_1$ and $R_3$ groups can be converted into other $R_1$ and $R_3$ groups.

It is possible, in particular, to convert an $R_1$ group, for example, by treating the product with solvolyzing, thermolyzing, esterifying, interesterifying, reducing, oxidizing or salt-forming agents, into another $R_1$ group.

Esters of Formula 1 ($R_1$ = $COOR_4$ or $CH_2OR_5$) can be converted, according to methods described in the literature, into the free carboxylic acids and/or the free alcohols by solvolysis, especially hydrolysis, and/or by thermolysis. The conditions of the solvolysis, especially hydrolysis (saponification) of these esters are ordinarily the same as in the solvolysis of the compounds of Formula 2h. Preferably, the esters are treated for about 1–48 hours with $K_2CO_3$ in methanol, ethanol or isopropanol at temperatures of between about 20° and 80°.

By dry heating of, in particular, tertiary alkyl esters of Formula 1 ($R_1$ = COO-tert.alkyl) to temperatures of between about 50° and 350°, acids of Formula 1 are obtained ($R_1$ = COOH). It is also possible to conduct the thermolysis in an inert solvent, e.g., benzene, water, DMF, ethylene glycol, glycerin, DMSO, cyclohexanol, preferably with the addition of catalytic amounts of an acid, e.g., p-toluenesulfonic acid.

The carboxylic acids 1 ($R_1$ = COOH) and/or the alcohols 1 ($R_1$ = $CH_2OH$) yield the respective esters 1 ($R_1$ = $COOR_4$ and $CH_2OR_5$, respectively) when proceeding in accordance with methods described in the literature. Thus, an acid of Formula 1 ($R_1$ = COOH) can be reacted with the respective alcohol $R_4OH$ or an alcohol of Formula 1 ($R_1$ = $CH_2OH$) can be reacted with the respective carboxylic acid $R_5OH$, for example in the presence of an inorganic or organic acid, e.g., HCl, HBr, HI, $H_2SO_4$, $H_3PO_4$, trifluoroacetic acid, a sulfonic acid, e.g., benzenesulfonic acid or p-toluenesulfonic acid, or an acidic ion exchanger, and also, if desired, in the presence of an inert solvent, e.g., benzene, toluene or xylene, at temperatures of between about 0° and preferably the boiling temperature.

The water of reaction can be removed azeotropically. Advantageously, a hydrocarbon (e.g., benzene or toluene) or chlorinated hydrocarbon (e.g., chloroform or 1,2-dichloro-ethane) are added in this method. The esterification is accomplished under gentle conditions with the addition of carbodiimides (e.g., N,N'-dicyclohexylcarbodiimide), and in this procedure, inert solvents are employed, e.g., ether, dioxane, 1,2-dimethoxyethane, benzene, $CH_2Cl_2$, or $CHCl_3$, and bases, such as pyridine, can be added. The methyl esters or ethyl esters can also be produced by reacting the free acids with diazomethane or diazoethane, respectively, in an inert solvent, e/g., ether, benzene or methanol.

Esters of Formula 1 ($R_1$ = $COOR_4$ or $CH_2OR_5$) can also be produced by the reaction of metallic salts of the corresponding carboxylic acids 1 ($R_1$ = COOH) or $R_5OH$, preferably the alkali metal, lead or silver salt, with a halogenide of the formula $R_4Hal$ or Z—$CHR_2$—$CH_2Hal$, optionally in an inert solvent, e.g., ether, benzene, DMF, or petroleum ether, or with an alkyl chlorosulfite, for example, those of the formula A—O—SOCl, wherein the thus-obtained adducts are subsequently subjected to thermolysis.

It is also possible to convert the acids first of all into the halogenides, anhydrides or nitriles thereof, and then react these compounds with the respective alcohol, optionally in the presence of an acidic catalyst or a base, e.g., NaOH, KOH, $Na_2CO_3$, $K_2CO_3$ or pyridine. Preferably, an excess of the alcohol and/or an inert solvent are utilized, and temperatures of between 0° and the boiling temperature are employed in this reaction. Tertiary alkyl esters can be obtained, for example, from the acid chlorides and potassium tert.-alcoholates. Suitable solvents are inert organic solvents, e.g., ether, THF or benzene. Excess halogenides or anhydrides can likewise be used as the solvent. In a preferred mode of operation, the alcohol of Formula 1 ($R_1$ = $CH_2OH$) is reacted in a pyridine solution with the halogenide or anhydride of the acid to be esterified.

Alcohols of Formula 1 ($R_1$ = $CH_2OH$) can also be esterified with ketenes, preferably in an inert solvent, e.g., ether, benzene or toluene, and with the addition of an acidic catalyst, e.g., sulfuric acid or p-toluene-sulfonic acid.

Esters of Formula 1 ($R_1$ = $COOR_4$) can also be prepared by transesterification of other esters of Formula 1 ($R_1$ = $COOR_{15}$ wherein $R_{15}$ is any desired organic residue but preferably $CH_3$ or $C_2H_5$) with an excess of the respective alcohol, or by reacting the carboxylic acids 1 ($R_1$ = COOH) with any desired other esters of the respective alcohol, which esters are preferably utilized in an excess. Analogously, esters of Formula 1 ($R_1$ = $CH_2OR_5$) can be obtained by transesterification of alcohols of Formula 1 ($R_1$ = $CH_2OH$) with an excess of a lower fatty acid alkyl ester (e.g., of the formula $R_5$—$OR^4$).

The transesterification methods described in the literature are employed in this connection preferably in the presence of a basic or acidic catalyst, e.g., sodium ethylate or sulfuric acid, at temperatures of between about 0° and the boiling temperature.

It is also possible to convert a thus-obtained product of Formula 1 (for example with $R_1$ = COOH, $COOR_4$ or $CH_2OR_5$) into another product of Formula 1 (e.g., with $R_1$ = $CH_2OH$) by treatment with a reducing agent.

Alcohols of the formula Z—$CHR_2$—$CH_2OH$ can thus be obtained, for example, from acids of the formula Z—$CHR_2$—COOH or esters of the formula Z—$CHR_2$—$COOR_4$ or Z—$CHR_2$—$CH_2OR_5$ with $LiAlH_4$ or with sodium in ethanol. Details of the reducing methods are described hereinabove [Section (c)]. However, the conditions must be selected, in accordance with the disclosure in the literature, so that the SO— or $SO_2$— groups present in the molecule are not simultaneously reduced.

Conversely, it is also possible to oxidize thus-obtained alcohols Z—$CHR_2$—$CH_2OH$ to the corresponding carboxylic acids Z—$CHR_2$—COOH. Suitable oxidizing agents in this connection are chromic acid and/or the salts thereof, e.g., sodium dichromate, preferably in an aqueous-sulfuric acid medium and/or with the addition of acetone, acetic acid and/or benzene as the solvent; silver oxide, which can suitably be prepared in situ from silver nitrate and NaOH, preferably in an aqueous-alkaline medium; $KMnO_4$, e.g., in pyridine; $NiO_2$, e.g., in THF in the presence of a base, e.g., $Na_2CO_3$.

In a thus-produced compound of Formula 1, an $R_3$ group can be converted into another $R_3$ group by substitution reactions and/or further conversions of the introduced or already present substituents.

For example, it is possible according to methods described in the literature to introduce a halogen atom into the benzene ring of the heteroaromatic molecule by direct halogenation, or by successive nitration, reduction, diazotization and Sandmeyer reaction.

A chlorine or bromine atom can be introduced, for example, by direct reaction with elemental chlorine or bromine in an inert solvent, e.g., water, aqueous sodium hydroxide solution, ether, tetrachloromethane, acetic acid, without or with the addition of catalysts, e.g., iron fillings, iodine, $FeCl_3$, $AlCl_3$, $SbCl_3$ or $SnCl_4$, preferably between −30° and 100°; or by reaction in a strongly hydrochloric solution with $H_2O_2$ or with $NaClO_3$, wherein the chlorination is effected by the chlorine formed in the nascent state; or by reaction with $SO_2Cl_2$ in an inert solvent, e.g., chlorobenzene, in the presence of radical-forming catalysts, e.g., peroxides, at preferably 80°–180°; or by reaction with hypobromous acid, acyl hypobromites, N-bromoimides, e.g., N-bromosuccinimide, N-bromophthalimide, or other bromine-yielding agents, e.g., 1,3-dibromo-5,5-dimethyl-hydantoin, in an inert solvent, e.g., nitrobenzene or carbon disulfide, preferably at −10° to 150°.

Halogen atoms can also be introduced into the aromatic nucleus according to methods described in the literature by first nitrating a compound of Formula 1 ($R_3 = H$) (for example with nitric acid), reducing the thus-obtained nitro compound to the corresponding amino compound (e.g., by catalytic hydrogenation or with nascent hydrogen), and diazotizing this product, for example in a hydrochloric or hydrobromic aqueous solution by the addition of an inorganic nitrite, preferably $NaNO_2$ or $KNO_2$, at temperatures of between about −20° and +10°, or in an inert organic solvent, e.g., diethyl ether or diglyme, by the addition of an organic nitrite, e.g., n-butyl nitrite or isoamyl nitrite at temperatures of between −20° and +5°.

In order to introduce a fluorine atom, the diazotizing step is carried out, for example, in anhydrous hydrofluoric acid, and then the reaction mixture is heated, or the diazonium salts are reacted with $HBF_4$ to the sparingly soluble diazonium tetrafluoroborates which latter are isolated and can be converted by thermal methods, e.g., heating in an inert solvent, into the desired fluorine compounds.

The diazonium group is exchanged against chlorine or bromine preferably in a hot aqueous solution in the presence of $Cu_2Cl_2$ or $Cu_2Br_2$ according to the Sandmeyer method. The exchange against bromine can also be accomplished by reaction with bromine to obtain the diazonium perbromide and subsequent refluxing in solvents, e.g., water or lower alcohols.

The free carboxylic acids of Formula 1 ($R_1 = COOH$) can be converted into a physiologically acceptable metallic or ammonium salt by reaction with a base. Especially suitable salts are the sodium, potassium, magnesium, calcium and ammonium salts. Others are the substituted ammonium salts, such as, for example, the dimethyl- and diethylammonium and other di-lower-alkylammonium salts, monoethanol-, diethanol-, and triethanolammonium and other alkanolammonium salts, and cyclohexylammonium, dicyclohexylammonium and other cycloalkylammonium salts.

Conversely, the carboxylic acids can be liberated from the acid addition salts thereof by treatment with a strong base, e.g., sodium or potassium hydroxide, or with sodium or potassium carbonate.

The compounds of Formula 1 contain a center of asymmetry and are ordinarily present in the racemic form.

The racemates can be separated into their optical antipodes by methods indicated in the literature. The method of chemical separation is preferred. According to this process, diastereomers are formed from the racemic mixture by reaction with an optically active auxiliary agent. For example, diastereomeric salts of the compounds of Formula 1 ($R_1 = COOH$) can be formed with optically active amines, such as quinine, cinchonidine, brucine, cinchonine, morphine, 1-phenylethylamine, 1-naphthylethylamine, quinidine and strychnine. By hydrolytical decomposition of the isolated diastereomeric compound, optically active antipodes of the compounds of Formula 1 are also obtained. Furthermore, it is, of course, possible to obtain optically active compounds according to the above-described methods by utilizing starting substances which themselves are optically active.

The compounds of Formula 1 possess, with good compatibility, excellent antiphlogistic activity and have a favorable effect, in particular, on the chronically progressive disease processes on the joints. They also possess analgesic and antipyretic activity. The compounds of Formula 1 can, therefore, be employed as medicinal agents, especially for obtaining antiphlogistic and antirheumatic effects, as well as for alleviating pain and lowering the fever in living beings, and also as intermediates for the production of other medicinal agents.

The compounds of Formula 1 and/or the physiologically acceptable salts thereof can be utilized in a mixture with solid, liquid and/or semiliquid excipients as medicinal agents in the human or veterinary medicine. Suitable vehicles are those organic or inorganic materials feasible for parenteral, enteral or topical application and which do not react with the novel compounds, such as, for example, water, vegetable oils, benzyl alcohols, polyethylene glycols, gelatin, lactose, amylose, magnesium stearate, talc, vaseline, cholesterol. Especially suitable for parenteral application are, in particular, solutions, preferably oily or aqueous solutions, as well as suspensions, emulsions or implants. Suitable for enteral application are tablets, dragees, capsules, syrups, elixirs or suppositories, and for topical application, ointments, creams or powders. The above-indicated preparations can optionally be sterilized or can contain auxiliary agents, such as lubricants, preservatives, stabilizers or wetting agents, emulsifiers, salts to influence the osmotic pressure, buffers, coloring, flavoring and/or aromatic materials.

The substances are preferably administered in dosages of between 1 and 500 mg. per dosage unit.

A particularly preferred dosage range is between 20 and 300 mg. per dosage unit. The daily dosage is preferably between 0.02 and 10 mg per kg body weight. The oral application is preferred.

The antiphlogistic effect of the compounds can be shown, f.e., by the method of Newbould as described in Brit. J. Pharmacol. vol. 21 (1963), pages 127 to 136, on rats.

The temperatures are indicated hereinabove and hereinbelow in degrees Celsius. "Worked up as usual" means the following: Water is added, if necessary; the mixture is extracted with ethyl acetate, ether or chloroform, separated, the organic extract washed with water, dried over sodium sulfate, filtered, the solvent is distilled off, and the residue is purified by distillation or crystallization. DMF = dimethylformamide, DMSO = dimethyl sulfoxide, THF = tetrahydrofuran.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

1.5 g. of methyl iodide is added to a mixture, agitated for 15 minutes at 20°, consisting of 3.44 g. of the tert.-butyl ester 5(or 10)-oxide of 2-thianthrenylacetic acid (obtainable by reacting 2-thianthrenylacetyl chloride with potassium tert.-butylate and subsequent oxidation with $H_2O_2$), 0.3 g. of NaH, and 20 ml. of 1,2-dimethoxyethane; this mixture is stirred for 12 hours at 20°, then diluted with ether, and worked up as usual, thus obtaining the tert.-butyl ester 5(or 10)-oxide of 2-(2-thianthrenyl)-propionic acid. The thus-obtained crude product is heated for 30 minutes to 260°, the product being 2-(2-thianthrenyl)-propionic acid 5(or 10)-oxide, dicyclohexylammonium salt, m.p. 178°–180°.

EXAMPLE 2

After agitation for 15 minutes at 20°, a mixture of 3.02 g. of the methyl ester 10,10-dioxide of 2-thioxanthenylacetic acid (obtainable by oxidation of the methyl ester of 2-thioxanthenylacetic acid) and 0.25 g. of NaH in 15 ml. of 1,2-dimethoxyethane is combined with 2.5 g. of methyl iodide. The mixture is allowed to stand for several hours, worked up as usual, and the product is the methyl ester 10,10-dioxide of 2-(2-thioxanthenyl)-propionic acid.

EXAMPLE 3

At −20°, a dry $CO_2$ stream is introduced into a solution of 1-(2-phenoxathiinyl)-ethyllithium 10,10-dioxide [obtainable by adding dropwise 3.5 ml. of a 20% solution of n-butyllithium in hexane to a solution of 3.39 g. of 2-(1-bromoethyl)-phenoxathiin 10,10-dioxide in 30 ml. of absolute ether at −60° and agitation for one-half hour at −60°]. After 2 hours, the mixture is poured into water, acidified, and worked up as usual, thus obtaining 2-(2-phenoxathiinyl)-propionic acid 10,10-dioxide, m.p. 161°–162°.

2-(1-Bromoethyl)-phenoxathiin 10,10-dioxide can be obtained by reducing 2-acetylphenoxathiin 10,10-dioxide with $NaBH_4$ to 2-(1-hydroxyethyl)-phenoxathiin 10,10-dioxide and subsequent reaction with HBr in benzene.

EXAMPLE 4

1.2 g. of magnesium filings and 1.2 g. of magnesium powder are heated under agitation in 60 ml. of absolute ether; a moderately dry $CO_2$-stream is introduced into the reaction mixture, a grain of iodine is added thereto, and a solution of 2.96 g. of 2-(1-chloroethyl)-thianthrene 5(or 10)-oxide (obtainable from 2-(1-hydroxyethyl)-thianthrene 5(or 10)-oxide and $SOCl_2$) in 20 ml. of absolute ether is added dropwise thereto. The mixture is refluxed for 20 minutes, cooled, filtered, evaporated, and water is added thereto, after which the mixture is worked up as usual, thus obtaining 2-(2-thianthrenyl)-propionic acid 5(or 10)-oxide; dicyclohexylammonium salt, m.p. 178°–180°.

EXAMPLE 5

A solution of 3.39 g. of 2-(1-bromoethyl)-phenoxathiin 10,10-dioxide in 20 ml. of THF is gradually added under agitation to a mixture of 0.26 g. of magnesium powder and 20 ml. of THF at 45°. The solution is stirred for another 15 minutes, filtered, poured on 1 kg. of solid carbon dioxide, allowed to warm up to 20°, the solvent removed, and the mixture worked up as usual, thus producing 2-(2-phenoxathiinyl)-propionic acid 10,10-dioxide, m.p. 161°–162°.

The starting material employed can also be equivalent amounts of
1-(2-phenoxathiinyl)-1-ethylmagnesium iodide 10,10-dioxide,
1-(2-phenoxathiinyl)-1-ethylmagnesium chloride 10,10-dioxide,
1-(2-phenoxathiinyl)-1-ethyllithium 10,10-dioxide,
1-(2-phenoxathiinyl)-1-ethylzinc 10,10-dioxide,
1-(2-phenoxathiinyl)-1-ethylcadmium 10,10-dioxide,
1-(2-phenoxathiinyl)-1-ethylsodium 10,10-dioxide, or
1-(2-phenoxathiinyl)-1-ethylpotassium 10,10-dioxide.

EXAMPLE 6

2 g. of the tetraethyl ester of orthocarbonic acid is added to a solution of 1-(2-phenoxathiinyl)-1-ethylmagnesium bromide 10,10-dioxide (prepared from 3.39 g. of 2-(1-bromoethyl)-phenoxathiin 10,10-dioxide) in 30 ml. of THF, and the mixture is agitated for 4 hours at 25°. An excess of semiconcentrated hydrochloric acid is gradually added thereto, the mixture is refluxed for 24 hours, allowed to cool, and worked up as usual, thus obtaining 2-(2-phenoxathiinyl)-propionic acid 10,10-dioxide, m.p. 161°–162°.

EXAMPLE 7

A Grignard solution produced from 3.39 g. of 2-(1-bromoethyl)-phenoxathiin 10,10-dioxide in 20 ml. of THF is gradually added to a solution of 1.2 g. of ethyl chloroformate in 20 ml. of THF. To this mixture is added 15 ml. of concentrated hydrochloric acid, the mixture is refluxed for 24 hours, and worked up as usual, thus producing 2-(2-phenoxathiinyl)-propionic acid 10,10-dioxide, m.p. 161°–162°.

EXAMPLE 8 a. A mixture of 2.9 g. of 2-(2-phenoxathiinyl)-2-propanol 10,10-dioxide (obtainable from 2-acetylphenoxathiin and $CH_3MgI$ with subsequent hydrolysis and oxidation), 1 g. of sulfur, and 1.74 g. of morpholine is refluxed for 18 hours. The excess morpholine is removed under reduced pressure, and the residue is refluxed with 10 ml. of concentrated hydrochloric acid and 10 ml. of acetic acid for 4 hours. The mixture is then poured into water and worked up as usual, thus obtaining 2-(2-phenoxathiinyl)-propionic acid 10,10-dioxide, m.p. 161°–162°.

As the starting material, equivalent quantities of 2-(2-propenyl)-phenoxathiin 10,10-dioxide or 2-(2-phenoxathiinyl)-1,2-propylene oxide 10,10-dioxide can also be employed.

b. 3.04 g. of 2-(2-phenoxathiinyl)-propionic acid 10,10-dioxide is dissolved in a mixture of 10 ml. of dioxane, 0.56 g. of KOH, and 4 ml. of water and then combined under agitation at 5°–7° dropwise with a solution of 1.6 g. of bromine in 16 ml. of dioxane (duration about 30 minutes). The mixture is evaporated, the residue is dissolved in 15 ml. of water, and worked up as usual, thus producing 2-(8-bromo-2-phenoxathiinyl)-propionic acid 10,10-dioxide, m.p. 231°–232°.

Analogously, the corresponding bromine compounds of Formula 1 are obtained from the corresponding unsubstituted compounds by means of bromination, for example:
2-(7-bromo-2-thianthrenyl)-propionic acid 5,5,10,10-tetroxide.

c. A solution of 3.04 g. of 2-(2-phenoxathiinyl)-propionic acid 10,10-dioxide in a small amount of ether is treated with dry chlorine; the progression of the chlorination is followed by means of thin-layer chromatography. After termination of the reaction, the mixture is filtered, the filtrate is evaporated, and the residue is chromatographed on silica gel, thus obtaining 2-(8-chloro-2-phenoxathiinyl)-propionic acid 10,10-dioxide.

d. A solution of 3.04 g. of 2-(2-phenoxathiinyl)-propionic acid 10,10-dioxide in 60 ml. of acetic acid is treated with 0.38 g. of chlorine at 25°–30°. After the usual working-up step, 2-(8-chloro-2-phenoxathiinyl)-propionic acid 10,10-dioxide is produced.

EXAMPLE 9

A solution of 2.72 g. of 2-(2-propenyl)-phenoxathiin 10,10-dioxide (obtainable by the reaction of 2-acetylphenoxathiin with $CH_3MgI$, hydrolysis, splitting off water, and oxidation) in 20 ml. of ether is treated with a solution of diborane in THF, until an analysis by thin-layer chromatography indicates the end of the reaction. The mixture is thereafter treated at 0° with 2 g. of $CrO_3$ in 10 ml. of water and, within 30 minutes, 2 ml. of acetic acid is added in incremental portions. After two hours of agitation at 20°, the mixture is diluted with water and worked up as usual, thus obtaining 2-(2-phenoxathiinyl)-propionic acid 10,10-dioxide, m.p. 161°–162°.

EXAMPLE 10

2.56 g. of 2-(2-propenyl)-thianthrene 5(or 10)-oxide [obtainable from 2-acetylthianthrene] is dissolved in 5 ml. of diglyme and combined with 3 ml. of a 1-molar solution of $NaBH_4$ in diglyme. Under agitation and introduction of $N_2$, a solution of 0.56 g. of freshly distilled $BF_3$ etherate in 1.2 ml. of diglyme is added slowly and dropwise within 30 minutes to this solution. The reaction mixture is then combined with 0.7 ml. of water, and 2.8 ml. of a 3N NaOH solution, as well as 2.8 ml. of 30% $H_2O_2$ are added dropwise at 80°–100°. The mixture is cooled, mixed with ice water, worked up as usual, and 2-(2-thianthrenyl)-propanol 5(or 10)-oxide is thus produced.

EXAMPLE 11

3.53 g. of 2-(1-bromo-2-propyl)-phenoxathiin 10,10-dioxide is reacted with 0.26 g. of Mg filings in 100 ml. of ether. The reaction mixture is cooled to −5°, oxygen is introduced for 4 hours, and the mixture combined with aqueous $NH_4Cl$ solution. The usual working-up step yields 2-(2-phenoxathiinyl)-propanol 10,10-dioxide, m.p. 92°–93°.

EXAMPLE 12

2.88 g. of 2-(2-phenoxathiinyl)-propanal 10,10-dioxide [obtainable from 2-(2-phenoxathiinyl)-acrylic acid ethyl ester 10,10-dioxide and $LiAlH_4$ in THF at 20°] is cooled to 0° in a mixture of 50 ml. of acetic acid and 50 ml. of benzene and combined under agitation and within 10 minutes with a solution of 0.63 g. of $CrO_3$ in 2.5 ml. of water and 50 ml. of acetic acid. After stirring for 1 hour at 25°, 25 ml. of methanol is added thereto; the mixture is then diluted with water and extracted with ether. The ether phase is extracted with 4% NaOH and the alkaline extracts worked up as usual, thus obtaining 2-(2-phenoxathiinyl)-propionic acid 10,10-dioxide, m.p. 161°–162°.

EXAMPLE 13 a. One gram of crude 2-(2-phenoxathiinyl)-acrylic acid 10,10-dioxide [obtainable by refluxing the corresponding ethyl ester with aqueous-ethanolic KOH] is dissolved in 25 ml. of dioxane, mixed with 0.1 g. of $PtO_2$, and hydrogenated at 20° and under normal pressure until the hydrogen absorption is terminated. The reaction mixture is filtered and evaporated, thus producing 2-(2-phenoxathiinyl)-propionic acid 10,10-dioxide, m.p. 161°–162°.

b. One gram of 2-(2-phenoxathiinyl)-propionic acid 10,10-dioxide is allowed to stand for 24 hours at room temperature in 15 ml. of methanolic hydrochloric acid. The mixture is then evaporated and worked up as usual, yielding the methyl ester 10,10-dioxide of 2(2-phenoxathiinyl)-propionic acid.

Analogously (reaction times up to 3 days), it is possible to produce, from the corresponding acids by reaction with HCl in methanol, ethanol, n-propanol, isopropanol, n-butanol, isobutanol, sec.-butanol, n-pentanol, isopentanol, n-hexanol, n-heptanol, n-octanol and 2-ethylhexanol, respectively, the corresponding products: methyl, ethyl, n-propyl, isopropyl, n-butyl, isobutyl, sec.-butyl, n-pentyl, isopentyl, n-hexyl, n-heptyl, n-octyl, and 2-ethylhexyl esters, e.g. the 5,5,10,10-tetroxide of methyl ester, ethyl ester, n-propyl ester, isopropyl ester, n-butyl ester, isobutyl ester, sec.-butyl ester, n-pentyl ester, isopentyl ester, n-hexyl ester, n-heptyl ester, n-octyl ester and 2-ethylhexyl ester of 2-(2-thianthrenyl)-propionic acid; as well as the 10,10-dioxide of the methyl ester, ethyl ester, n-propyl ester, isopropyl ester, n-butyl ester, isobutyl ester, sec.-butyl ester, n-pentyl ester, isopentyl ester, n-hexyl ester, n-heptyl ester, n-octyl ester and 2-ethylhexyl ester of 2-(2-thioxanthenyl)-propionic acid; as well as the 10,10-dioxide of the ethyl ester (b.p. 233°–237°/0.2 mm.), n-propyl ester, isopropyl ester, n-butyl ester, isobutyl ester, sec.-butyl ester, n-pentyl ester, isopentyl ester, n-hexyl ester, n-heptyl ester, n-octyl ester and 2-ethylhexyl ester of 2-(2-phenoxathiinyl)-propionic acid.

c. 3.04 g. of 2-(2-phenoxathiinyl)-propionic acid 10,10-dioxide is refluxed for 7 hours with 1 ml. of concentrated $H_2SO_4$ and 30 ml. of n-butanol. The mixture is evaporated, taken up in chloroform, washed with $NaHCO_3$ solution, dried, and evaporated, thus producing 2-(2-phenoxathiinyl)-propionic acid n-butyl ester 10,10-dioxide.

EXAMPLE 14 a. 3.48 g. of the 10,10-dioxide of the ethyl ester of 2-(2-phenoxathiinyl)-2-hydroxypropionic acid [obtainable by reacting phenoxathiin with ethoxalyl chloride, reaction of the thus-obtained ethyl ester of 2-phenoxathiinylglyoxylic acid with $CH_3MgI$ in ether to obtain the ethyl ester of 2-(2-phenoxathiinyl)-2-hydroxypropionic acid, and oxidation with $H_2O_2$] is dissolved in 50 ml. of xylene; 0.1 g. of p-toluenesulfonic acid is added thereto and the mixture refluxed for 3½ hours with the use of a water trap. After cooling, the mixture is washed with sodium bicarbonate solution and water, separated, dried over sodium sulfate, and concentrated by evaporation. The thus-produced oily ethyl ester 10,10-dioxide of 2-(2-phenoxathiinyl)-acrylic acid is dissolved in 30 ml. of ethanol and hydrogenated on 4% palladium charcoal at 50° and 6 atmospheres until the hydrogen absorption has ceased (3 hours). The mixture is filtered and evaporated, thus obtaining the ethyl ester 10,10-dioxide of 2-(2-phenoxathiinyl)-propionic acid.

b. 3.32 g. of the ethyl ester 10,10-dioxide of 2-(2-phenoxathiinyl)-propionic acid is refluxed with 1 g. of KOH in 25 ml. of ethanol for 2 hours. The mixture is evaporated, the residue is dissolved in water, washed with ether, acidified with hydrochloric acid to pH 3, and worked up as usual, yielding 2-(2-phenoxathiinyl)-propionic acid 10,10-dioxide, m.p. 161°–162°.

c. One gram of the ethyl ester 10,10-dioxide of 2-(2-phenoxathiinyl)-propionic acid is refluxed for 90 minutes in a mixture of 8 ml. of acetic acid and 8 ml. of 25% hydrochloric acid. After working up the mixture as usual, 2-(2-phenoxathiinyl)-propionic acid 10,10-dioxide is obtained, m.p. 161°–162°.

d. A mixture of 1 g. of the ethyl ester 10,10-dioxide of 2-(2-phenoxathiinyl)-propionic acid and 100 ml. of water is heated in an autoclave for 24 hours to 180°. The mixture is cooled, worked up as usual, and the product is 2-(2-phenoxathiinyl)-propionic acid 10,10-dioxide, m.p. 161°–162°.

e. At 0°, a solution of 0.7 g. of $NaNO_2$ in 2 ml. of water is added dropwise to a solution of 3.19 g. of 2-(7-amino-2-phenoxathiinyl)-propionic acid 10,10-dioxide [obtainable by the oxidizing nitration of 2-(2-phenoxathiinyl)-propionic acid and subsequent reduction] in 25 ml. of 15% hydrochloric acid. Thereafter, 1.12 ml. of a 40% $HBF_4$ solution is added dropwise. The mixture is buffered to pH 5–6, the thus-precipitated diazonium tetrafluoroborate is filtered, washed with water, dried, and introduced in incremental portions into 20 ml. of boiling xylene. After the decomposition reaction has ceased, the product is concentrated by evaporation and worked up as usual, yielding 2-(7-fluoro-2-phenoxathiinyl)-propionic acid 10,10-dioxide.

Analogously, the corresponding amino compounds yield the following products:
2-(6-fluoro-2-thioxanthenyl)-propionic acid 10,10-dioxide,
2-(7-fluoro-2-thianthrenyl)-propionic acid 5,5,10,10-tetroxide,
2-(7-fluoro-2-phenoxathiinyl)-butyric acid 10,10-dioxide.

f. 3.19 g. of 2-(7-amino-2-phenoxathiinyl)-propionic acid 10,10-dioxide is dissolved in 20 ml. of water and 7 ml. of concentrated hydrochloric acid and then combined, at 0°–5°, with 0.7 g. of $NaNO_2$ in 2 ml. of water, whereupon the mixture is slowly added dropwise to a hot $Cu_2Cl_2$ solution (obtained by the reduction of 2.1 g. of $CuSO_4$ with $SO_2$ in 13 ml. of water in the presence of 2.6 g. of NaCl), further heated for 30 minutes to 90°–95°, cooled, saturated with $H_2S$, and filtered. The filtrate is worked up as usual, yielding 2-(7-chloro-2-phenoxathiinyl)-propionic acid 10,10-dioxide.

Analogously, the following products are obtained from the corresponding amino compounds:
2-(6-chloro-2-thioxanthenyl)-propionic acid 10,10-dioxide,
2-(7-chloro-2-thianthrenyl)-propionic acid 5,5,10,10-tetroxide,
2-(7-chloro-2-phenoxathiinyl)-butyric acid 10,10-dioxide.

g. 3.19 g. of 2-(7-amino-2-phenoxathiinyl)-propionic acid 10,10-dioxide is dissolved in 12 ml. of water and 1.2 ml. of concentrated $H_2SO_4$, combined dropwise with a solution of 0.7 g. of $NaNO_2$ in 2 ml. of water at 0.5°, added dropwise to a boiling solution of 0.66 g. of $CuSO_4 \cdot 5H_2O$, 1.54 g. of NaBr, and 0.2 g. of copper powder (previously refluxed for 4 hours and then mixed with 25 mg. of $Na_2SO_3$) heated for 30 minutes to 95°, cooled, saturated with $H_2S$, filtered, and the filtrate worked up as usual, thus obtaining 2-(7-bromo-2-phenoxathiinyl)-propionic acid 10,10-dioxide.

Analogously, the following products are obtained from the corresponding amino compounds:
2-(6-bromo-2-thioxanthenyl)-propionic acid 10,10-dioxide,
2-(7-bromo-2-thianthrenyl)-propionic acid 5,5,10,10-tetroxide,
2-(7-bromo-2-phenoxathiinyl)-butyric acid 10,10-dioxide.

EXAMPLE 15 a. A solution of 3.2 g. of 2-(2-phenoxathiinyl)-2-hydroxypropionic acid 10,10-dioxide (obtainable by reacting 2-acetylphenoxathiin with sodium cyanide and benzoyl chloride in THF to 2-(2-phenoxathiinyl)-2-benzoyloxypropionitrile, oxidation to the sulfone with $H_2O_2$, and hydrolysis with HCl/acetic acid) in 30 ml. of acetic acid is hydrogenated on 0.2 g. of 10% Pd/C in the presence of 0.01 ml. $HClO_4$ at 20° and under normal pressure. The mixture is filtered, diluted with water, and the product is 2-(2-phenoxathiinyl)-propionic acid 10,10-dioxide, m.p. 161°–162°.

With the same success, the following can also be employed as starting materials: the 10,10-dioxide of 2-(2-phenoxathiinyl)-2-acetoxypropionic acid, 2-(2-phenoxathiinyl)-2-chloropropionic acid, 2-(2-phenoxathiinyl)-2-bromopropionic acid, 2-(2-phenoxathiinyl 2-iodopropionic acid, or 2-(2-phenoxathiinyl)-2-methoxypropionic acid, respectively.

b. One gram of 2-(2-phenoxathiinyl)-propionic acid 10,10-dioxide is dissolved in 10 ml. of THF and under agitation such a quantity of ethereal diazomethane solution is added dropwise until no evolution of nitrogen can be observed any longer. After 20 minutes, the reaction mixture is concentrated by evaporation, yielding the methyl ester 10,10-dioxide of 2-(2-phenoxathiinyl propionic acid.

EXAMPLE 16

3.48 g. of the ethyl ester 10,10-dioxide of 2-(2-phenoxathiinyl)-2-hydroxypropionic acid is dissolved in 40 ml. of acetic acid and introduced into a solution of 9 g. of $SnCl_2 \cdot 2H_2O$ in 20 ml. of concentrated hydrochloric acid. The mixture is refluxed for 3 hours, buffered with sodium hydroxide solution to pH 2, and then hydrogen sulfide is introduced until the precipitation of SnS has ceased. The mixture is filtered and worked up as usual, thus producing 2-(2-phenoxathiinyl)-propionic acid 10,10-dioxide, m.p. 161°–162°.

EXAMPLE 17 a. A mixture of 18 g. of 2-(2-phenoxathiinyl)-2-hydroxypropionic acid ethyl ester 10,10-dioxide, 4.7 g. of potassium iodide, 2.8 g. of red phosphorus, and 24 ml. of 85% phosphoric acid is heated under agitation to 130° for 7 hours. The mixture is worked up as usual, thus obtaining the ethyl ester 10,10-dioxide of 2-(2-phenoxathiinyl)-propionic acid, b.p. 233°–237°/0.2 mm.

Analogously, from the starting compounds set forth below, the corresponding des-hydroxy esters are obtained by reduction with $KI/P/H_3PO_4$:
ethyl ester 10,10-dioxide of 2-(2-thioxanthenyl)-2-hydroxypropionic acid,
ethyl ester 10,10-dioxide of 2-(8-bromo-2-phenoxathiinyl)-2-hydroxypropionic acid,
ethyl ester 5,5,10,10-tetroxide of 2-(2-thianthrenyl)-2hydroxypropionic acid.

b. A solution of 3.32 g. of the ethyl ester 10,10-dioxide of 2-(2-phenoxathiinyl)-propionic acid in 25 ml. of absolute THF is added dropwise to a suspension of 0.38 g. of LiAlH₄ in 15 ml. of THF. The mixture is agitated for 30 minutes and then a mixture of 2 ml. of THF, 0.5 ml. of water, and 1 ml. of 32% sodium hydroxide solution is added dropwise thereto under ice cooling. The mixture is filtered over kieselguhr, dried, and evaporated, yielding 2-(2-phenoxathiinyl)-propanol 10,10-dioxide, m.p. 92°–93°.

Analogously, the following products are obtained by reduction of the corresponding esters with LiAlH₄:
2-(2-thianthrenyl)-propanol 5,5,10,10-tetroxide
2-(7-fluoro-2-thianthrenyl)-propanol 5,5,10,10-tetroxide
2-(8-fluoro-2-thianthrenyl)-propanol 5,5,10,10-tetroxide
2-(7-chloro-2-thianthrenyl)-propanol 5,5,10,10-tetroxide
2-(8-chloro-2-thianthrenyl)-propanol 5,5,10,10-tetroxide
2-(7-bromo-2-thianthrenyl)-propanol 5,5,10,10-tetroxide
2-(8-bromo-2-thianthrenyl)-propanol 5,5,10,10-tetroxide
2-(2-thianthrenyl)-butanol 5,5,10,10-tetroxide
2-(2-thioxanthenyl)-propanol 10,10-dioxide
2-(7-fluoro-2-thioxanthenyl)-propanol 10,10-dioxide
2-(7-chloro-2-thioxanthenyl)-propanol 10,10-dioxide
2-(7-bromo-2-thioxanthenyl)-propanol 10,10-dioxide
2-(2-thioxanthenyl)-1-butanol 10,10-dioxide
2-(8-fluoro-2-phenoxathiinyl)-propanol 10,10-dioxide
2-(8-chloro-2-phenoxathiinyl)-propanol 10,10-dioxide
2-(8-bromo-2-phenoxathiinyl)-propanol 10,10-dioxide
2-(2-phenoxathiinyl)-1-butanol 10,10-dioxide.

c. One gram of 2-(2-phenoxathiinyl)-propanol 10,10-dioxide is allowed to stand for 24 hours in 5 ml. of pyridine and 5 ml. of acetic anhydride. The mixture is concentrated, worked up as usual, and the product is 2-(2-phenoxathiinyl)-propyl acetate 10,10-dioxide, b;p. 233°–237°/0.2 mm.

Analogously, the corresponding acetates are obtained from the corresponding alcohols, for example:
2-(2-thianthrenyl)-propyl acetate 5,5,10,10-tetroxide
2-(7-fluoro-2-thianthrenyl)-propyl acetate 5,5,10,10-tetroxide
2-(8-fluoro-2-thianthrenyl)-propyl acetate 5,5,10,10-tetroxide
2-(7-chloro-2-thianthrenyl)-propyl acetate 5,5,10,10-tetroxide
2-(8-chloro-2-thianthrenyl)-propyl acetate 5,5,10,10-tetroxide
2-(7-bromo-2-thianthrenyl)-propyl acetate 5,5,10,10-tetroxide
2-(8-bromo-2-thianthrenyl)-propyl acetate 5,5,10,10-tetroxide
2-(2-thianthrenyl)-1-butyl acetate 5,5,10,10-tetroxide
2-(2-thioxanthenyl)-propyl acetate 10,10-dioxide
2-(7-fluoro-2-thioxanthenyl)-propyl acetate 10,10-dioxide
2-(7-chloro-2-thioanthenyl)-propyl acetate 10,10-dioxide
2-(7-bromo-2-thioxanthenyl)-propyl acetate 10,10-dioxide
2-(2-thioxanthenyl)-1-butyl acetate 10,10-dioxide
2-(8-fluoro-2-phenoxathiinyl)-propyl acetate 10,10-dioxide
2-(8-chloro-2-phenoxathiinyl)-propyl acetate 10,10-dioxide
2-(8-bromo-2-phenoxathiinyl)-propyl acetate 10,10-dioxide
2-(2-phenoxathiinyl)-1-butyl acetate 10,10-dioxide.

With the use of propionic acid anhydride or butyric acid anhydride, respectively, the corresponding propionates andd butyrates, respectively, are analogously obtained, for example:
2-(2-thianthrenyl)-propyl propionate 5,5,10,10-tetroxide
2-(2-thianthrenyl)-propyl butyrate 5,5,10,10-tetroxide
2-(2-thioxanthenyl)-propyl propionate 10,10-dioxide
2-(2-thioxanthenyl)-propyl butyrate 10,10-dioxide
2-(2-phenoxathiinyl)-propyl propionate 10,10-dioxide
2-(2-phenoxathiinyl)-propyl butyrate 10,10-dioxide.

EXAMPLE 18

3.48 g. of the ethyl ester 10,10-dioxide of 2-(2-phenoxathiinyl) -2-hydroxypropionic acid is dissolved in 10 ml. of dichloromethane, saturated with dry HCl gas, and mixed with 1 ml. of SOCl₂. The reaction mixture is heated for 2 hours to 50° and the solvent is removed. The residue, consisting of the ethyl ester 10,10-dioxide of 2-(2-phenoxathiinyl)-2-chloropropionic acid, is dissolved in 100 ml. of methanol and hydrogenated on 100 mg. of platinum oxide under normal pressure and at 25°. The reaction mixture is then filtered off, the filtrate combined with a solution of 0.4 g. of NaOH in 5 ml. of water, refluxed for 2 hours, evaporated, the residue dissolved in water, and the reaction mixture worked up as usual, thus obtaining 2-(2-phenoxathiinyl)-propionic acid 10,10-dioxide, m.p. 161°–162°.

EXAMPLE 19

3.3 g. of the ethyl ester 10,10-dioxide of 2-(2-phenoxathiinyl)-acrylic acid is refluxed together with 0.4 g. of LiAlH₄ in 40 ml. of absolute THF for 15 hours. Thereafter, the mixture is combined with 4 ml. of 25% NaOh solution, the THF phase is decanted off, the residue is washed twice with ether, and the combined organic phases are dried and evaporated. The residue is dissolved in 40 ml. of absolute THF, 0.4 g. of LiAlH₄ is added thereto, and the mixture is again refluxed for 8 hours. After the usual working-up step, 2-(2-phenoxathiinyl)-propanol 10,10-dioxide is obtained, m.p. 92°–92°.

EXAMPLE 20

3.66 g. of the ethyl ester 10,10-dioxide of 2-chloro-2-(2-phenoxathiinyl)-propionic acid is dissolved in 40 ml. of absolute ether and gradually added dropwise to a suspension of 1.1 g. of LiAlH₄ in 50 ml. of ether. The reaction mixture is refluxed for several hours, methanol is added, and the mixture is worked up as usual, yielding 2-(2-phenoxathiinyl)-propanol 10,10-dioxide, m.p. 92°–93°.

EXAMPLE 21

9 ml. of a 1-molar ether-LiAlH₄ solution is added to a suspension of 5.4 g. of anhydrous AlCl₃ in 30 ml. of absolute ether. Within one hour, a solution of 2.88 g. of 1-methyl-1-(2-phenoxathiinyl)-ethylene oxide 10,10-dioxide (obtainable by reacting 2-isopropenylphenoxathiin with N-bromosuccinimide in the aqueous phase to the corresponding bromohydrin, splitting off HBr with sodium hydroxide solution, and oxidation with H₂O₂) in 40 ml. of absolute ether is added dropwise to this reaction mixture. The latter is refluxed for 2 hours, hydrolyzed by adding 5 ml. of water and 50 ml. of 10% sulfuric acid, and worked up as usual, thus obtaining 2-(2-phenoxathiinyl)-propanol 10,10-dioxide, m.p. 92°–93°.

EXAMPLE 22

3.21 g. of 2-(2-phenoxathiinyl)-acryloyl chloride 10,10-dioxide (obtainable from the acid with $SOCl_2$ in benzene) is added dropwise under agitation to a suspension of 0.4 g. of $LiAlH_4$ in 30 ml. of ether at 20°. The mixture is stirred for 3 hours at 20°, then methanol is added, and the mixture is worked up as usual, thus producing 2-(2-phenoxathiinyl)-propanol 10,10-dioxide m.p. 92°–93°.

EXAMPLE 23

3.06 g. of 2-(2-phenoxathiinyl)-propane-1,2-diol 10,10-dioxide [obtainable by reducing the ethyl ester of 2-hydroxy-2-(2phenoxathiinyl)-propionic acid with $LiAlH_4$ and subsequent oxidation with $H_2O_2$] is hydrogenated in 50 ml. of methanol on 0.2 g. of $CuCr_2O_4$ catalyst at 100 atmospheres and 140°. The mixture is then cooled, filtered, and evaporated, thus obtaining 2-(2-phenoxathiinyl)-propanol 10,10-dioxide, m.p. 92°–93°.

EXAMPLE 24

2.88 g. of 2-(2-phenoxathiinyl)-propanal 10,10-dioxide is dissolved in 10 ml. of ethanol and added dropwise to a solution of 0.6 g. of $NaBH_4$ in 15 ml. of ethanol. The mixture is agitated for 2 hours at 20°, and then worked up as usual, obtaining 2-(2-phenoxathiinyl)-propanol 10,10-dioxide, m.p. 92°–93°.

EXAMPLE 25

A solution of 2.88 g. of 2-(2-phenoxathiinyl)-propanol 10,10-dioxide in 20 ml. of anhydrous THF is treated at −75° with a solution of 0.6 g. of $LiAlH_4$ in 20 ml. of anhydrous THF. The mixture is allowed to warm up to 20°, and is then decomposed with ethyl acetate and worked up as usual, yielding 2-(2-phenoxathiinyl)-propanol 10,10-dioxide, m.p. 92°–93°.

EXAMPLE 26 a. 2 g. of 2-(2-phenoxathiinyl)-propylbenzyl ether 10,10-dioxide [obtainable by reacting 1-bromo-2-(2-phenoxathiinyl)-propane with sodium benzylate in DMF and subsequently oxidizing the product with $H_2O_2$] is dissolved in 25 ml. of methanol and hydrogenated on 0.2 g. of 5% Pd/C catalyst at 20° until the hydrogen absorption has ceased. The reaction mixture is filtered off, evaporated, and the product is 2-(2-phenoxathiinyl)-propanol 10,10-dioxide, m.p. 92°–93°.

b. Silver oxide, freshly prepared from 6.4 g. of $AgNO_3$ and 1.6 g. of NaOH in 50 ml. of water is added to a mixture of 5.72 g. of 2-(2-phenoxathiinyl)-propanol 10,10-dioxide and 4 g. of NaOH in 40 ml. of water. The mixture is refluxed for 2 hours, the thus-precipitated silver is filtered off, the filtrate is worked up as usual, and the product is 2-(2-phenoxathiinyl)-propionic acid 10,10-dioxide. m.p. 161°–162°.

EXAMPLE 27

Two grams of the diethyl ester 5,5,10,10-tetroxide of 2-(2-thianthrenyl)-2-methylmalonic acid [obtainable by reacting the ethyl ester of 2-thianthrenylacetic acid with the diethyl ester of oxalic acid to the diethyl ester of 2-(2-thianthrenyl)-3-oxosuccinic acid, decarbonylation to the diethyl ester of 2-thianthrenylmalonic acid, methylation with methyl iodide, and oxidation with $H_2O_2$] is refluxed for 3 hours with 30 ml. of 10% ethanolic KOH solution. The ethanol is distilled off, the residue is introduced into 60 ml. of water, and the mixture is acidified to pH 4 with hydrochloric acid. The thus-precipitated 2-(2-thianthrenyl)-2-methylmalonic acid 5,5,10,10-tetroxide is filtered off, dried, dissolved in acetone, the solution is filtered and evaporated, and the residue is heated until the cessation of $CO_2$ liberation to 100°–120°/20 mm., thus obtaining 2-(2-thianthrenyl)-propionic acid 5,5,10,10-tetroxide, m.p. 228°–231°.

EXAMPLE 28

A solution of crude 2-(2-thianthrenyl)-2-methylmalonic acid 5,5,10,10-tetroxide [obtainable by saponification of 2 g. of the diethyl ester 5,5,10,10-tetroxide of 2-(2-thianthrenyl)-2-methylmalonic acid with ethanolic KOH under $N_2$] in 20 ml. of acetic acid and 20 ml. of 15% HCl is refluxed under $N_2$ until the evolution of $CO_2$ has ceased. After cooling and working up the mixture as usual, 2-(2-thianthrenyl)-propionic acid 5,5,10,10-tetroxide is obtained, m.p. 228°–231°.

EXAMPLE 29

One gram of the monoethyl ester 5,5,10,10-tetroxide of 2-(2-thianthrenyl)-2-methylmalonic acid [obtainable by partial saponification of the diethyl ester with 1 mole of KOH in ethanol and acidification] is gradually heated at 18 torr [mm. Hg] to 100°–130° until the liberation of $CO_2$ has ceased, yielding 2-(2-thianthrenyl)-propionic acid ethyl ester 5,5,10,10-tetroxide.

EXAMPLE 30

One gram of the ethyl ester 10,10-dioxide of 2-(2-thioxanthenyl)-2-methylbutan-3-onic acid [obtained by condensation of the ethyl ester of 2-thioxanthenylacetic acid with ethyl acetate to the ethyl ester of 2-(2-thioxanthenyl)-butan-+3-onic acid, methylation with methyl iodide, and oxidation with $H_2O_2$] is agitated for 45 minutes at 90° under $N_2$ with 15 ml. of 50% KOH, The reaction mixture is cooled, water and HCl are added to pH 10, the mixture is washed with ether, and worked up as usual, thus obtaining 2-(2-thioxanthenyl)-propionic acid 10,10-dioxide, m.p. 178°–180°.

EXAMPLE 31

A mixture of 3.39 g. of 2-(1-bromoethyl)-phenoxathiin 10,10-dioxide, 40 ml. of tert.-butanol, 2.3 g. of potassium tert.-butylate, and 10 g. of nickel carbonyl is heated for 24 hours to 50° and then evaporated to dryness. To this mixture is added 40 ml. of 6N hydrochloric acid, and the mixture is refluxed for 12 hours and worked up as usual, thus producing 2-(2-phenoxathiinyl)-propionic acid 10,10-dioxide, m.p. 161°–162°.

EXAMPLE 32

Within 20 minutes, 4 ml. of formic acid is added to a solution of 2.58 g. of 2-vinylphenoxathiin 10,10-dioxide [obtainable by splitting off water from 2-(1-hydroxyethyl)-phenoxathiin 10,10-dioxide with polyphosphoric acid] in a mixture of 12 ml. of sulfuric acid and 8 ml. of trifluoroacetic acid. After another 20 minutes, the mixture is poured into water, thus obtaining 2-(2-phenoxathiinyl)-propionic acid 10,10-dioxide, m.p. 161°–162°.

EXAMPLE 33

2.76 g. of 2-(1-hydroxyethyl)-phenoxathiin 10,10-dioxide [or 2.58 g. of 2-vinylphenoxathiin 10,10-dioxide] is dissolved in 10 ml. of 3% ethanolic hydrochloric acid; 20 mg. of $[(C_6H_5)_3P]_2PdCl_2$ is added thereto, and the mixture is heated under CO at 500 atmospheres in an autoclave for 5 hours to 85°. After cooling and the usual working-up step, the ethyl ester 10,10-dioxide of 2-(2-phenoxathiinyl)-propionic acid is obtained, b.p. 233°–237°/0.2 mm.

EXAMPLE 34

A mixture of 2.58 g. of 2-vinylphenoxathiin 10,10-dioxide [or 2.76 g. of 2-(1-hydroxyethyl)-phenoxathiin 10,10-dioxide], 2 ml. of nickel carbonyl, 2 ml. of concentrated hydrochloric acid, and 20 ml. of acetone is heated for 12 hours to 50° under irradiation with the light of a mercury vapor lamp. The mixture is then evaporated to dryness, the residue is extracted with ether and worked up as usual, yielding 2-(2-phenoxathiinyl)-propionic acid 10,10-dioxide, m.p. 161°–162°.

EXAMPLE 35

A mixture of 3.22 g. of 2-(2-chloropropionyl)-thianthrene 5(or 10)-oxide [obtainable by reaction of thianthrene with 2-chloropropionyl chloride in the presence of $AlCl_3$ and subsequent oxidation with $H_2O_2$], 0.8 g. of extremely fine-grained NaOH, and 50 ml. of toluene is refluxed under agitation for 30 hours. The mixture is then cooled, water is added thereto, and the mixture is worked up as usual, yielding 2-(2-thianthrenyl)-propionic acid 5(or 10)-oxide.

EXAMPLE 36

2.89 g. of 2-(2-phenoxathiinyl)-propylamine 10,10-dioxide [obtainable from 2-(2-phenoxathiinyl)-propionamide 10,10-dioxide with $LiAlH_4$] is dissolved in 50 ml. of 15% aqueous acetic acid and combined, under ice cooling, with a solution of 1 g. of $NaNO_2$ in 5 ml. of water. The mixture is heated for 1 hour to 80°, worked up as usual, and chromatographic purification on silica gel yields 2-(2-phenoxathiinyl)-propanol 10,10-dioxide.

EXAMPLE 37

3.53 g. of 1-bromo-2-(2-phenoxathiinyl)-propane 10,10-dioxide is dissolved in 20 ml. of DMF, combined with 3 g. of anhydrous potassium acetate, and agitated for 3 hours at 60°. The mixture is worked up as usual, thus obtaining 2-(2-phenoxathiinyl)-propyl acetate 10,10-dioxide, m.p. 78°.

EXAMPLE 38

One gram of 2-(2-phenoxathiinyl)-propionitrile 10,10-dioxide [obtainable from 2-(1-bromoethyl)-phenoxathiin 10,10-dioxide and KCN] is refluxed for 40 hours in 15 ml. of ethanol and 2 ml. of water with 2 g. of KOH. The mixture is then evaporated and the residue worked up as usual, thus producing 2-(2-phenoxathiinyl)-propionic acid 10,10-dioxide, m.p. 161°–162°.

Analogously, the corresponding acids are obtained with aqueous-ethanolic KOH with the use of the following starting compounds:
2-(2-thianthrenyl)-propionitrile 5,5,10,10-tetroxide
2-(7-fluoro-2-thianthrenyl)-propionitrile 5,5,10,10-tetroxide
2-(7-chloro-2-thianthrenyl)-propionitrile 5,5,10,10-tetroxide
2-(7-bromo-2-thianthrenyl)-propionitrile 5,5,10,10-tetroxide
2-(8-fluoro-2-thianthrenyl)-propionitrile 5,5,10,10-tetroxide
2-(8-chloro-2-thianthrenyl)-propionitrile 5,5,10,10-tetroxide
2-(8-bromo-2-thianthrenyl)-propionitrile 5,5,10,10-tetroxide 2-(2-thioxanthenyl)-propionitrile 10,10-dioxide
2-(7fluoro-2-thioxanthenyl)-propionitrile 10,10-dioxide
2-(7-chloro-2-thioxanthenyl)-propionitrile 10,10-dioxide
2-(7-bromo-2-thioxanthenyl)-propionitrile 10,10-dioxide
2-(8-fluoro-2-phenoxathiinyl)-propionitrile 10,10-dioxide
2-(8-chloro-2-phenoxathiinyl)-propionitrile 10,10-dioxide
2-(8-bromo-2-phenoxathiinyl)-propiontrile 10,10-dioxide.

EXAMPLE 39

One gram of 2-(2-phenoxathiinyl)-propionitrile 10,10-dioxide is refluxed under nitrogen for 2 hours with 6 ml. of acetic acid and 6 ml. of concentrated hydrochloric acid. The mixture is evaporated, the residue is dissolved in dilute NaOH, washed with ether, and worked up as usual, thus obtaining 2-(2-phenoxathiinyl)-propionic acid 10,10-dioxide, m.p. 161–162°.

EXAMPLE 40

One gram of 2-(2-phenoxathiinyl)-propionitrile 10,10-dioxide is refluxed for 48 hours with 3 ml. of n-hexanol and 0.1 g. of concentrated $H_2SO_4$. To this mixture is added 3 ml. of water, and the mixture is refluxed for another 48 hours and worked up as usual, thus producing 2-(2-phenoxathiinyl)-propionic acid 10,10-dioxide, m.p. 161°–162°.

EXAMPLE 41

One gram of 2-(2-phenoxathiinyl)-propionic acid 10,10-dioxide iminoethyl ether hydrochloride [obtainable from 2-(2-phenoxathiinyl)-propionitrile 10,10-dioxide and ethanol/HCL in ether at 0°] is refluxed for 1 hour with 25 ml. of water. After the usual working-up step, the ethyl ester 10,10-dioxide of 2-(2-phenoxathiinyl)-propionic acid is obtained, b.p. 233°–237°/0.2 mm.

EXAMPLE 42

3.04 g. of 2-(2-phenoxathiinyl)-propionamide 10,10-dioxide [obtainable from the nitrile and sulfuric acid at 25°] and 5 g. of KOH is refluxed in 100 ml. of ethanol under $N_2$ for 3 hours. The mixture is evaporated, worked up as usual, and the product is 2-(2-phenoxathiinyl)-propionic acid 10,10-dioxide, m.p. 161°–162°.

EXAMPLE 43

A mixture of 1 g. of 2-(2-phenoxathiinyl)-propionamide 10,10-dioxide, 2 ml. of concentrated hydrochloric acid, and 2 ml. of acetic acid is refluxed for 48 hours and, after the addition of water, worked up as usual, thus yielding 2-(2-phenoxathiinyl)-propionic acid 10,10-dioxide, m.p. 161°–162°.

EXAMPLE 44

3.5 g. of the ehtyl ester of 2-[3-(o-hydroxyphenylsulfonyl)-4-hydroxyphenyl]-propionic acid is heated with 0.7 g. of ZnCl₂ for 2 hours to 170°. After working up the mixture as usual, 2-(2-phenoxathiinyl)-propionic acid ethyl ester 10,10-dioxide is obtained, b.p. 233°–237°/0.2 mm.

EXAMPLE 45

3.2 g. of 2-[3-(o-aminophenylsulfonyl)-4-aminophenyl]-propionic acid is diazotized in dilute hydrochloric acid with 1.4 g. of NaNO₂. The mixture is allowed to stand for 15 minutes and then heated until the liberation of nitrogen has ceased, on a water bath. As the intermediate product, 2-[3-(o-hydroxyphenyl-sulfonyl)-4-hydroxyphenyl]-propionic acid is obtained which is not isolated. After the usual working-up operation, 2-(2-phenoxathiinyl)-propionic acid 10,10-dioxide is produced, m.p. 161°–162°.

EXAMPLE 46

A mixture of 3.4 g. of 2-[3-(o-hydroxyphenylsulfonyl)-4-chlorophenyl]-propionic acid, 0.6 g. of KOH, and 0.1 g. of Cu powder is heated for 5 hours to 190°. After cooling and the usual working-up step, 2-(2-phenoxathiinyl)-propionic acid 10,10-dioxide is obtained.

Analogously, 2-[3-(o-chlorophenylsulfonyl)-4-hydroxyphenyl]-propionic acid can be reacted to yield the analogous product.

EXAMPLE 47

A solution of 3.68 g. of a mixture consisting of the ethyl ester of 2-(3-chlorosulfonyl-4-phenoxyphenyl)-propionic acid and the ethyl ester of 2-(4-o-chlorosulfonylphenoxyphenyl)-propionic acid [obtainable by sulfonation of the ethyl ester of 2-(4-phenoxyphenyl)-propionic acid and subsequent reaction with POCl₃] in 100 ml. of 1,1,2,2-tetrachloroethane is combined with 3 g. of AlCl₃, and the mixture is heated for 2 hours to 100°. The mixture is then poured on ice, worked up as usual, and the product is the ethyl ester 10,10-dioxide of 2-(2-phenoxathiinyl)-propionic acid, b.p. 233°–237°/0.2 mm.

EXAMPLE 48

6 ml. of 30% H₂O₂ is added to a boiling solution of 2.88 g. of 2-(2-thianthrenyl)-propionic acid in 50 ml. of ethanol; the mixture is refluxed for 3 hours. After adding another 4 ml. of the oxidizing agent, the mixture is refluxed for another 9 hours, cooled, and worked up as usual, yielding 2-(2-thianthrenyl)-propionic acid 5(or 10)-oxide; dicyclohexylammonium salt, m.p. 178°–180°.

Analogously, with the use of the following starting compounds:

2-(2-thianthrenyl)-propionic acid methyl ester
2-(2-thianthrenyl)-propionic acid ethyl ester
2-(7-fluoro-2-thianthrenyl)-propionic acid
2-(7-fluoro-2-thianthrenyl)-propionic acid ethyl ester
2-(8-fluoro-2-thianthrenyl)-propionic acid
2-(8-fluoro-2-thianthrenyl)-propionic acid ethyl ester
2-(7-chloro-2-thianthrenyl)-propionic acid
2-(7-chloro-2-thianthrenyl)-propionic acid ethyl ester
2-(8-chloro-2-thianthrenyl)-propionic acid
2-(8-chloro-2-thianthrenyl)-propionic acid ethyl ester
2-(7-bromo-2-thianthrenyl)-propionic acid
2-(7-bromo-2-thianthrenyl)-propionic acid ethyl ester
2-(8-bromo-2-thianthrenyl)-propionic acid
2-(8-bromo-2-thianthrenyl)-propionic acid ethyl ester
2-(2-thianthrenyl)-butyric acid
2-(2-thianthrenyl)-butyric acid ethyl ester
2-(2-thianthrenyl)-propanol
2-(2-thianthrenyl)-propyl acetate
2-(2-thioxanthenyl)-propionic acid
2-(2-thioxanthenyl)-propionic acid ethyl ester
2-(7-fluoro-2-thioxanthenyl)-propionic acid
2-(7-fluoro-2-thioxanthenyl)-propionic acid ethyl ester
2-(7-chloro-2-thioxanthenyl)-propionic acid
2-(7-chloro-2-thioxanthenyl)-propionic acid ethyl ester
2-(7-bromo-2-thioxanthenyl)-propionic acid
2-(7-bromo-2-thioxanthenyl)-propionic acid ethyl ester
2-(2-thioxanthenyl)-butyric acid
2-(2-thioxanthenyl)-butyric acid ethyl ester
2-(2-thioxanthenyl)-propanol
2-(2-thioxanthenyl)-propyl acetate
2-(2-phenoxathiinyl)-propionic acid
2-(2-phenoxathiinyl)-propionic acid ethyl ester
2-(2-phenoxathiinyl)-butyric acid
2-(2-phenoxathiinyl)-butyric acid ethyl ester
2-(2-phenoxathiinyl)-propanol
2-(2-phenoxathiinyl)-propyl acetate
2-(2-phenoxathiinyl)-propyl propionate
2-(2-phenoxathiinyl)-propyl butyrate
2-(8-fluoro-2-phenoxathiinyl)-propionic acid
2-(8-fluoro-2-phenoxathiinyl)propionic acid ethyl ester
2-(8-chloro-2-phenoxathiinyl)-propionic acid
2-(8-chloro-2-phenoxathiinyl)-propionic acid ethyl ester
2-(8-bromo-2-phenoxathiinyl)-propionic acid
2-(8-bromo-2-phenoxathiinyl)-propionic acid ethyl ester
2-(8-bromo-2-phenoxathiinyl)-propanol
2-(8-bromo-2-phenoxathiinyl)-propyl acetate the following final products can be obtained by oxidation:

2-(2-thianthrenyl)-propionic acid methyl ester 5(or 10)-oxide
2-(2-thianthrenyl)-propionic acid ethyl ester 5(or 10)-oxide, b.p. 220°–224°/0.1 mm.
2-(7-fluoro-2-thianthrenyl)-propionic acid 5(or 10)-oxide
2-(7-fluoro-2-thianthrenyl)-propionic acid ethyl ester 5(or 10)-oxide
2-(8-fluoro-2-thianthrenyl)-propionic acid 5(or 10)-oxide
2-(8-fluoro-2-thianthrenyl)-propionic acid ethyl ester 5(or 10)-oxide
2-(7-chloro-2-thianthrenyl)-propionic acid 5(or 10)-oxide
2-(7-chloro-2-thianthrenyl)-propionic acid ethyl ester 5(or 10)-oxide
2-(8-chloro-2-thianthrenyl)-propionic acid 5(or 10)-oxide
2-(8-chloro-2-thianthrenyl)-propionic acid ethyl ester 5(or 10)-oxide
2-(7-bromo-2-thianthrenyl)-propionic acid 5(or 10)-oxide
2-(7-bromo-2-thianthrenyl)-propionic acid ethyl ester 5(or 10)-oxide
2-(8-bromo-2-thianthrenyl)-propionic acid 5(or 10)-oxide 2-(8-bromo-2-thianthrenyl)-propionic acid ethyl ester 5(or 10)-oxide
2-(2-thianthrenyl)-butyric acid 5(or 10)-oxide
2-(2-thianthrenyl)-butyric acid ethyl ester 5(or 10)-oxide
2-(2-thianthrenyl)-propanol 5-or 10)-oxide
2-(2-thianthrenyl)-propyl acetate 5(or 10)-oxide
2-(2-thioxanthenyl)-propionic acid 10-oxide
2-(2-thioxanthenyl)-propionic acid ethyl ester 10-oxide
2-(7-fluoro-2-thioxanthenyl)-propionic acid 10-oxide
2(7-fluoro-2-thioxanthenyl)-propionic acid ethyl ester 10-oxide
2-(7-chloro-2-thioxanthenyl)-propionic acid 10-oxide
2-(7-chloro-2-thioxanthenyl)-propionic acid ethyl ester 10-oxide
2-(7-bromo-2-thioxanthenyl)-propionic acid 10-oxide
2-(7-bromo-2-thioxanthenyl)-propionic acid ethyl ester 10-oxide
2-(2-thioxanthenyl)-butyric acid 10-oxide
2-(2-thioxanthenyl)-butyric acid ethyl ester 10-oxide
2-(2-thioxanthenyl)-propanol 10-oxide
2-(2-thioxanthenyl)-propyl acetate 10-oxide
2-(2-phenoxathiinyl)-propionic acid 10-oxide, m.p. 171°–172°
2-(2-phenoxathiinyl)-propionic acid ethyl ester 10-oxide
2-(2-phenoxathiinyl)-butyric acid 10-oxide
2-(2-phenoxathiinyl)-butyric acid ethyl ester 10-oxide
2-(2-phenoxathiinyl)-propanol 10-oxide
2-(2-phenoxathiinyl)-propyl acetate 10-oxide
2-(2-phenoxathiinyl)-propyl propionate 10-oxide
2-(2-phenoxathiinyl)-propyl butyrate 10-oxide 2-(8-fluoro-2-phenoxathiinyl)-propionic acid 10-oxide
2-(8-fluoro-2-phenoxathiinyl)-propionic acid ethyl ester 10-oxide
2-(8-chloro-2-phenoxathiinyl)-propionic acid 10-oxide
2-(8-chloro-2-phenoxathiinyl)-propionic acid ethyl ester 10-oxide
2-(8-bromo-2-phenoxathiinyl)-propionic acid 10-oxide
2-(8-bromo-2-phenoxathiinyl)-propionic acid ethyl ester 10-oxide
2-(8-bromo-2-phenoxathiinyl)-propanol 10-oxide
2-(8-bromo-2-phenoxathiinyl)-propyl acetate 10-oxide.

EXAMPLE 49

9 ml. of 30% $H_2O_2$ is added to a warm solution of 2.72 g. of 2-(2-phenoxathiinyl)-propionic acid in 10 ml. of acetic acid, and the mixture is refluxed for 90 minutes. Working up the mixture as usual yields 2-(2-phenoxathiinyl)-propionic acid 10,10-dioxide, m.p. 161°–162°.

Analogously, the following compounds are obtained from the corresponding thio ethers by oxidation with excess $H_2O_2$ in acetic acid:
2-(2-thianthrenyl)-propionic acid 5,5,10,10-tetroxide, m.p. 228°–231°
2-(2-thianthrenyl)-propionic acid methyl ester 5,5,10,10-tetroxide
2-(2-thianthrenyl)-propionic acid ethyl ester 5,5,10,10tetroxide
2-(7-2-thianthrenyl)-propionic acid 5,5,10,10-tetroxide
2-(7-fluoro-2-thianthrenyl)-propionic acid ethyl ester 5,5,10,10-tetroxide
2-(8-fluoro-2-thianthrenyl)-propionic acid 5,5,10,10-tetroxide
2-(8-fluoro-2-thianthrenyl)-propionic acid ethyl ester 5,5,10,10-tetroxide
2-(7-chloro-2-thianthrenyl)-propionic acid 5,5,10,10-tetroxide
2-(7-chloro-2-thianthrenyl)-propionic acid ethyl ester 5,5,10,10-tetroxide
2-(8-chloro-2-thianthrenyl)-propionic acid ethyl ester 5,5,10,10-tetroxide
2-(7-bromo-2-thianthrenyl)-propionic acid 5,5,10,10-tetroxide
2-(7-bromo-2-thianthrenyl)-propionic acid ethyl ester 5,5,10,10-tetroxide
2-(8-bromo-2-thianthrenyl)-propionic acid 5,5,10,10-tetroxide
2-(8-bromo-2-thianthrenyl)-propionic acid ethyl ester 5,5,10,10-tetroxide
2-(2-thianthrenyl)-butyric acid 5,5,10,10-tetroxide
2-(2-thianthrenyl)-butyric acid ethyl ester 5,5,10,10-tetroxide
2-(2-thianthrenyl)-propanol 5,5,10,10-tetroxide
2-(2-thianthrenyl)-propyl acetate 5,5,10,10-tetroxide
2-(2-thioxanthenyl)-propionic acid 10,10-dioxide, m.p. 178°–180°
2-(2-thioxanthenyl)-propionic acid ethyl ester 10,10-dioxide
2-(7-fluoro-2-thioxanthenyl)-propionic acid 10,10-dioxide
2-(7-fluoro-2-thioxanthenyl)-propionic acid ethyl ester 10,10-dioxide
2-(7-chloro-2-thioxanthenyl)-propionic acid 10,10-dioxide
2-(7-chloro-2-thioxanthenyl)-propionic acid ethyl ester 10,10-dioxide
2-(7-bromo-2-thioxanthenyl)-propionic acid 10,10-dioxide
2-(7-bromo-2-thioxanthenyl)-propionic acid ethyl ester 10,10-dioxide
2-(2-thioxanthenyl)-butyric acid 10,10-dioxide
2-(2-thioxanthenyl)-butyric acid 10,10-dioxide
2-(2-thioxanthenyl)-butyric acid ethyl ester 10,10-dioxide
2-(2-thioxanthenyl)-propanol 10,10-dioxide
2-(2-thioxanthenyl)-propyl acetate 10,10-dioxide 2-(2-phenoxathiinyl)-propionic acid 10,10-dioxide
2-(2-phenoxathiinyl)-propionic acid ethyl ester 10,10-dioxide, b.p. 233°–237°/0.2 mm.
2-(2-phenoxathiinyl)-butyric acid 10,10-dioxide
2-(2-phenoxathiinyl)-butyric acid ethyl ester 10,10-dioxide
2-(2-phenoxathiinyl)-propanol 10,10-dioxide
2-(2-phenoxathiinyl)-propyl acetate 10,10-dioxide, m.p. 78°
2-(2-phenoxathiinyl)-propyl propionate 10,10-dioxide
2-(2-phenoxathiinyl)-propyl butyrate 10,10-dioxide
2-(8-fluoro-2-phenoxathiinyl)-propionic acid 10,10-dioxide, m.p. 174°–176°
2-(8-fluoro-2-phenoxathiinyl)-propionic acid ethyl ester 10,10-dioxide
2-(8-chloro-2-phenoxathiinyl)-propionic acid 10,10-dioxide
2-(8-chloro-2-phenoxathiinyl)-proponic acid ethyl ester 10,10-dioxide
2-(8-bromo-2-phenoxathiinyl)-propionic acid 10,10-dioxide, m.p. 231°–232°
2-(8-bromo-2-phenoxathiinyl)-propionic acid ethyl ester 10,10-dioxide, m.p. 73°–75°
2-(8-bromo-2-phenoxathiinyl)-propanol 10,10-dioxide, m.p. 162°–164°

2-(8-bromo-2-phenoxathiinyl)-propyl acetate 10,10-dioxide, m.p. 108°–110°.

EXAMPLE 50

Within 30 minutes and at 75°–80°, a solution of 2.38 ml. of 30% $H_2O_2$ in 70 ml. of acetic acid is added dropwise under agitation to a solution of 2.88 g. of 2-(2-thianthrenyl)-propionic acid in 100 ml. of acetic acid. The mixture is maintained at 80° for 2 hours, boiled up, poured into water, and worked up as usual, thus obtaining 2-(2-thianthrenyl)-propionic acid 5,10-dioxide (mixture of stereoisomers).

Analogously, the following compounds are produced from the corresponding thianthrenes:

2-(2-thianthrenyl)-propionic acid methyl ester 5,10-dioxide
2-(2-thianthrenyl)-propionic acid ethyl ester 5,10-dioxide
2-(7-fluoro-2-thianthrenyl)-propionic acid 5,10-dioxide
2-(7-fluoro-2-thianthrenyl)-propionic acid ethyl ester 5,10-dioxide
2-(8-fluoro-2-thianthrenyl)-propionic acid 5,10-dioxide
2-(8-fluoro-2-thianthrenyl)-propionic acid ethyl ester 5,10-dioxide
2-(7-chloro-2-thianthrenyl)-propionic acid 5,10-dioxide
2-(7-chloro-2-thianthrenyl)-propionic acid ethyl ester 5,10-dioxide
2-(8-chloro-2-thianthrenyl)-propionic acid 5,10-dioxide
2-(8-chloro-2-thianthrenyl)-propionic acid ethyl ester 5,10-dioxide
2-(7-bromo-2-thianthrenyl)-propionic acid 5,10-dioxide
2-(7-bromo-2-thianthrenyl)-propionic acid ethyl ester 5,10-dioxide
2-(8-bromo-2-thianthrenyl)-propionic acid 5,10-dioxide
2-(8-bromo-2-thianthrenyl)-propionic acid ethyl ester 5,10-dioxide
2-(2-thianthrenyl)-butyric acid 5,10-dioxide
2-(2-thianthrenyl)-butyric acid ethyl ester 5,10-dioxide
2-(2-thianthrenyl)-propanol 5,10-dioxide
2-(2-thianthrenyl)-propyl acetate 5,10-dioxide.

EXAMPLE 51 a. Within 40 minutes, a solution of 3.4 ml. of 30% $H_2O_2$ in 100 ml. of acetic acid is added dropwise under agitation at 75°–80° to a solution of 2.88 g. of 2-(2-thianthrenyl)-propionic acid in 100 ml. of acetic acid. The reaction mixture is maintained for 2 hours at 80°, boiled up, poured into water, and worked up as usual, thus obtaining 2-(2-thianthrenyl)-propionic acid 5,5,10(or 5,10,10)-trioxide.

Analogously, the following final products are obtained from the corresponding thianthrenes:

2-(2-thianthrenyl)-propionic acid methyl ester 5,5,10(or 5,10,10)-trioxide
2-(2-thianthrenyl)-propionic acid ethyl ester 5,5,10(or 5,10,10)-trioxide
2-(7-fluoro-2-thianthrenyl)-propionic acid 5,5,10(or 5,10,10)-trioxide
2-(7-fluoro-2-thianthrenyl)-propionic acid ethyl ester 5,5,10(or 5,10,10)-trioxide
2-(8-fluoro-2-thianthrenyl)-propionic acid 5,5,10(or 5,10,10)-trioxide
2-(8-fluoro-2-thianthrenyl)-propionic acid ethyl ester 5,5,10(or 5,10,10)-trioxide
2-(7-chloro-2-thianthrenyl)-propionic acid 5,5,10(or 5,10,10)-trioxide
2-(7-chloro-2-thianthrenyl)-propionic acid ethyl ester 5,5,10(or 5,10,10)-trioxide
2-(8-chloro-2-thianthrenyl)-propionic acid 5,5,10(or 5,10,10)-trioxide
2-(8-chloro-2-thianthrenyl)-propionic acid ethyl ester 5,5,10(or 5,10,10)-trioxide
2-(7-bromo-2-thianthrenyl)-propionic acid 5,5,10(or 5,10,10)-trioxide
2-(7-bromo-2-thianthrenyl)-propionic acid ethyl ester 5,5,10(or 5,10,10)-trioxide
2-(8-bromo-2-thianthrenyl)-propionic acid 5,5,10(or 5,10,10)-trioxide
2-(8-bromo-2-thianthrenyl)-propionic acid ethyl ester 5,5,10(or 5,10,10)-trioxide
2-(2-thianthrenyl)-butyric acid 5,5,10(or 5,10,10)-trioxide
2-(2-thianthrenyl)-butyric acid ethyl ester 5,5,10(or 5,10,10)-trioxide
2-(2-thianthrenyl)-propanol 5,5,10(or 5,10,10)-trioxide
2-(2-thianthrenyl)-propyl acetate 5,5,10(or 5,10,10)-trioxide.

b. 3.36 g. of 2-(2-thianthrenyl)-propionic acid 5,5,10(or 5,10,10)-trioxide is dissolved in 20 ml. of acetic acid; the solution is combined with a solution of 1.62 g. of HBr in 10 ml. of acetic acid, poured into water, and the product thus obtained is 2-(2-thianthrenyl)-propionic acid 5,5(or 10,10)-dioxide.

Analogously, the following compounds are obtained from the corresponding trioxides:

2-(2-thianthrenyl)-propionic acid methyl ester 5,5(or 10,10)-dioxide
2-(2-thianthrenyl)-propionic acid ethyl ester 5,5(or 10,10)-dioxide
2-(7-fluoro-2-thianthrenyl)-propionic acid 5,5(or 10,10)-dioxide
2-(7-fluoro-2-thianthrenyl)-propionic acid ethyl ester 5,5(or 10,10)-dioxide
2-(8-fluoro-2-thianthrenyl)-propionic acid 5,5(or 10,10)-dioxide
2-(8-fluoro-2-thianthrenyl)-propionic acid ethyl ester 5,5(or 10,10)-dioxide
2-(7-chloro-2-thianthrenyl)-propionic acid 5,5(or 10,10)-dioxide
2-(7-chloro-2-thianthrenyl)-propionic acid ethyl ester 5,5(or 10,10)-dioxide
2-(8-chloro-2-thianthrenyl)-propionic acid 5,5(or 10,10)-dioxide
2-(8-chloro-2-thianthrenyl)-propionic acid ethyl ester 5,5(or 10,10)-dioxide
2-(7-bromo-2-thianthrenyl)-propionic acid 5,5(or 10,10)-dioxide
2-(7-bromo-2-thianthrenyl)-propionic acid ethyl ester 5,5(or 10,10)-dioxide
2-(8-bromo-2-thianthrenyl)-propionic acid 5,5(or 10,10)-dioxide
2-(8-bromo-2-thianthrenyl)-propionic acid ethyl ester 5,5(or 10,10)-dioxide
2-(2-thianthrenyl)-butyric acid 5,5(or 10,10)-dioxide
2-(2-thianthrenyl)-butyric acid ethyl ester 5,5(or 10,10)-dioxide
2-(2-thianthrenyl)-propanol 5,5(or 10,10)-dioxide
2-(2-thianthrenyl)-propyl acetate 5,5(or 10,10)-dioxide.

EXAMPLE 52

Within 1.5 hours, 3.73 ml. of 33% HNO₃ is added to a boiling solution of 2.88 g. of 2-(2-thianthrenyl)-propionic acid in 35 ml. of acetic acid; the mixture is refluxed for another half hour, then cooled and worked up as usual, yielding 2-(2-thianthrenyl)-propionic acid 5(or 10)-oxide, dicyclohexylammonium salt, m.p. 178°-180°.

EXAMPLE 53

A mixture of 2.88 g. of 2-(2-thianthrenyl)-propionic acid, 3.75 g. of sodium dichromate, 18 ml. of acetic acid, and 6.65 ml. of 50% sulfuric acid is heated to 60° for 4 hours. After working up the mixture as usual, 2-(2-thianthrenyl)-propionic acid 5,5,10,10-tetroxide is obtained, m.p. 228°-231°.

As the starting material, it is also possible to employ the stoichiometric amounts of 2-(2-thianthrenyl)-propanol or 2-(2-thianthrenyl)-propanal, or the mono- or disulfoxides of these compounds, or 2-(2-thianthrenyl)-propionic acid 5,5(or 10,10)-dioxide.

EXAMPLE 54

Chlorine is introduced for one hour into a suspension of 2.88 g. of 2-(2-thianthrenyl)-propionic acid in 40 ml. of boiling 90% acetic acid. The mixture is then cooled, diluted with water, and worked up as usual, yielding 2-(2-thianthrenyl)-propionic acid 5,5,10(or 5,10,10)-trioxide.

EXAMPLE 55

A solution of 2.88 g. of 2-(2-thianthrenyl)-propionic acid in 75 ml. of absolute methanol is combined at 0°-5° in incremental portions with 1.75 g. of N-bromosuccinimide. The mixture is agitated for one hour at 0°-5°, then evaporated, extracted with ether, and the extract yields 2-(2-thianthrenyl)-propionic acid 5(or 10)-oxide.

EXAMPLE 56

At −78°, a solution of 1.45 g. of 1-chlorobenzotriazole in 5 ml. of methanol is added dropwise under agitation to a solution of 2.88 g. of 2-(2-thianthrenyl)-propionic acid in 100 ml. of methanol. Then the mixture is combined at room temperature with excess sodium bicarbonate solution, washed with methylene chloride, acidified, and worked up as usual, thus obtaining 2-(2-thianthrenyl)-propionic acid 5(or 10)-oxide.

EXAMPLE 57

2.88 g. of 2-(2-thianthrenyl)-propionic acid is dissolved in a mixture of 20 ml. of acetonitrile and 5 ml. of water and combined, under agitation at 20°, with 2.2 g. of (NH₄)₂Ce(NO₃)₆. After working up the mixture as usual, 2-(2-thianthrenyl)-propionic acid 5(or 10)-oxide is obtained.

EXAMPLE 58

A diazonium salt solution prepared from 1.52 g. of o-nitroaniline and 0.011 mole of nitrosylsulfuric acid in 20 ml. of acetic acid is added dropwise at 25° to an agitated mixture of 2.88 g. of 2-(2-thianthrenyl)-propionic acid and 30 ml. of acetic acid. The mixture is stirred for 12 hours at 25°, poured into water, and worked up as usual, yielding 2-(2-thianthrenyl)-propionic acid 5(or 10)-oxide.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

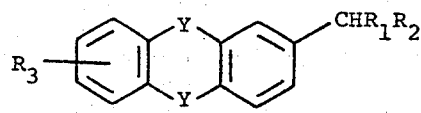

wherein $R_1$ is COOH, COOR₄, CH₂OH or CH₂OR₅; $R_2$ is CH₃ or C₂H₅; $R_3$ is F, Cl or Br; $R_4$ is alkyl of 1-8 carbon atoms; $R_5$ is alkanoyl of 2-4 carbon atoms; one of the Y groups is SO or SO₂ and the other Y group is CH₂, O, S, SO or SO₂; or a physiologically acceptable salt of those compounds wherein $R_1$ is COOH.

2. A compound of the formula

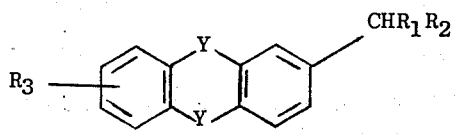

wherein $R_1$ is COOH or a physiologically acceptable salt thereof; $R_2$ is CH₃ or C₂H₅; $R_3$ is H, F, Cl or Br; one of the Y groups is SO or SO₂ and the other Y group is CH₂.

3. A compound of Claim 2, claim 2-(2-thioxanthenyl)-propionic acid 10,10-dioxide.

4. A compound of the formula

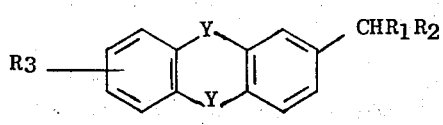

wherein $R_1$ is COOH or a physiologically acceptable salt thereof; $R_2$ is CH₃ or C₂H₅; $R_3$ is H, F, Cl or Br; one of the Y groups is SO or SO₂ and the other Y group is O.

5. A compound of claim 4, 2-(2-phenoxathiinyl)-propionic acid 10-oxide.

6. A compound of claim 4, 2-(2-phenoxathiinyl)-propionic acid 10,10-dioxide.

7. A compound of claim 4, 2-(8-bromo-2-phenoxathiinyl)-propionic acid 10,10-dioxide.

8. A compound of the formula

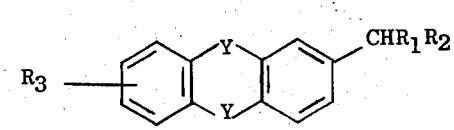

wherein $R_1$ is COOR₄; $R_2$ is CH₃ or C₂H₅; $R_3$ is H, F, Cl or Br; $R_4$ is alkyl of 1-8 carbon atoms; one of the Y groups is SO or SO₂ and the other Y group is O.

9. A compound of claim 8, 2-(2-phenoxathiinyl)-propionic acid ethyl ester 10,10-dioxide.

* * * * *